United States Patent [19]

Hofmeister et al.

[11] Patent Number: 5,389,624

[45] Date of Patent: Feb. 14, 1995

[54] ANTIANDROGENIC [3,2-C]PYRAZOLE AND [3,2-D]TRIAZOLE STEROIDS

[75] Inventors: Helmut Hofmeister; Dieter Bittler; Horst Michna; Ursula Habenicht; Karl-Heinrich Fritzemeier; Yukishige Nishino, all of Berlin, Germany

[73] Assignee: Schering Aktiengesellschaft, Berlin and Bergkamen, Germany

[21] Appl. No.: 52,976

[22] Filed: Apr. 27, 1993

Related U.S. Application Data

[62] Division of Ser. No. 725,330, Jul. 5, 1991, Pat. No. 5,236,912.

[30] Foreign Application Priority Data

Jul. 4, 1990 [DE] Germany ............................ 4021433

[51] Int. Cl.[6] ........................ A61K 31/58; C07J 71/00
[52] U.S. Cl. .................................... 514/176; 540/51
[58] Field of Search ........................ 540/51; 514/176

[56] References Cited

U.S. PATENT DOCUMENTS

| | | | |
|---|---|---|---|
| 3,280,112 | 10/1966 | Christiansen et al. | 540/51 |
| 3,290,293 | 12/1966 | Hirschmann | 260/239.5 |
| 3,704,295 | 11/1972 | Clinton | 260/239.5 |
| 4,297,350 | 10/1981 | Babcock et al. | 424/238 |
| 4,684,636 | 8/1987 | Christiansen et al. | 514/176 |

FOREIGN PATENT DOCUMENTS 0207375  1/1987  European Pat. Off. .

OTHER PUBLICATIONS

Chemical Abstracts, vol. 55, "10J–Steroids," 1961, pp. 14517–14520, abstract of Steroidal [3,2-c]pyrazoles. II. Androstanes, 19-nor-androstanes, and their unsaturated analogs, by R. O. Clinton et al.

Primary Examiner—Patricia L. Morris
Attorney, Agent, or Firm—Millen, White, Zelano, & Branigan

[57]  ABSTRACT

[3,2-c]Pyrazole and [3,2-d]triazole steroids are useful anti-androgens.

14 Claims, No Drawings

ANTIANDROGENIC [3,2-C]PYRAZOLE AND [3,2-D]TRIAZOLE STEROIDS

This is a divisional application of application Ser. No. 07/725,330, filed Jul. 5, 1991, now U.S. Pat. No. 5,236,912, issued Aug. 17, 1993.

The present invention relates to [3,2-c]pyrazole and [3,2-d]triazole steroids of general Formula I

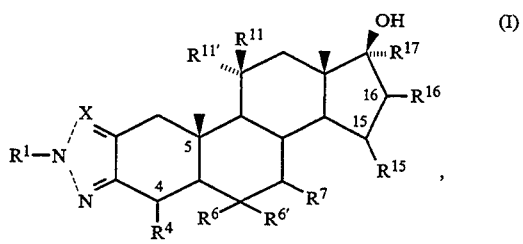

wherein
X is the group CH or a nitrogen atom,
$R^1$ is an alkylsulfonyl group R—$SO_2$— and, if X is the group CH, is additionally an acyl group R—CO— wherein R in each case means an alkyl group of 1–3 carbon atoms,

is a C—C single or double bond,
$R^4$ is a hydrogen atom or a methyl group that is in the α- or β-position in case of a C-4-C-5 single bond,
$R^6$ and $R^{6'}$ in each case mean a hydrogen atom or jointly a 6,6-methylene or ethylene group,
$R^7$ is a hydrogen atom or, if $R^6$ and $R^{6'}$ are respectively hydrogen atoms, additionally a saturated or unsaturated α- or β-alkyl group of 1–4 carbon atoms, or
$R^6$ and $R^7$ mean a 6α,7α- or 6β,7β-methylene group or an additional bond between the number 6 and 7 carbon atoms, and also
$R^{6'}$ is a hydrogen atom,
$R^{11}$ is a hydrogen, fluorine or chlorine atom, and
$R^{11'}$ is a hydrogen atom, or
$R^{11}$ and $R^{11'}$ jointly mean a methylene group,
$R^{15}$ and $R^{16}$ each mean a hydrogen atom,

means a C—C double bond, a 15α,16α- or 15β,16β-methylene group, or—if $R^6$ and $R^{6'}$ jointly mean a 6,6-ethylene, 6,6-methylene group, or $R^7$ stands for an alkyl group of 1–4 carbon atoms or X means a nitrogen atom—additionally means a C—C single bond, and also
$R^{17}$ is a hydrogen atom, an alkyl group of 1–4 carbon atoms, a vinyl, E- or Z-halovinyl (halogen: F, Cl, Br, I), allyl, ethynyl, bromoethynyl, chloroethynyl, or propynyl group, as well as to a process for the preparation thereof, to pharmaceutical preparations containing these steroid azoles of general Formula I, as well as to their usage for the production of medicinal agents.

The following compounds are preferred according to this invention:

1′-mesyl-17α-methyl-1′H-androsta-4,15-dieno[3,2-c]pyrazol-17β-ol,
4,17α-dimethyl-1′-mesyl-1′H-androsta-4,15-dieno[3,2-c]pyrazol-17β-ol,
17α-ethynyl-1′-mesyl-1′H-androsta-4,15-dieno[3,2-c]pyrazol-17β-ol,
17α-ethynyl-1′-mesyl-4-methyl-1′H-androsta-4,15-dieno[3,2-c]pyrazol-17β-ol,
17α-chloroethynyl-1′-mesyl-1′H-androsta-4,15-dieno[3,2-c]pyrazol-17β-ol,
17α-bromoethynyl-1′-mesyl-1′H-androsta-4,15-dieno[3,2-c]pyrazol-17β-ol,
1′-mesyl-17α-propyn-1-yl-1′H-androsta-4,15-dieno[3,2-c]pyrazol-17β-ol,
1′acetoxy-17α-methyl-1′H-androsta-4,15-dieno[3,2-c]pyrazol-17β-ol,
1′-acetoxy-4,17α-dimethyl-1′H-androsta-4,15-dieno[3,2-c]pyrazol-17β-ol,
1′-mesyl-17α-methyl-6-methylene-1′H-androsta-4,15-dieno[3,2-c]pyrazol-17β-ol,
1′-mesyl-17α-methyl-6-methylene-1′H-androst-4-eno[3,2-c]pyrazol-17β-ol,
6,6-ethylene-1′-mesyl-17α-methyl-1′H-androst-4-eno[3,2-c]pyrazol-17β-ol,
4,17α-dimethyl-1′-mesyl-6-methylene-1′H-androst-4-eno[3,2-c]pyrazol-17β-ol,
7α,17α-dimethyl-1′-mesyl-1′H-androst-4-eno[3,2-c]pyrazol-17β-ol,
1′-mesyl-4,7α,17α-trimethyl-1′H-androst-4-eno[3,2-c]pyrazol-17β-ol,
1′-mesyl-7α-methyl-17α-vinyl-1′H-androst-4-eno[3,2-c]pyrazol-17β-ol,
1′-mesyl-17α-methyl-15α,16α-methylene-1′H-androst-4-eno[3,2-c]pyrazol-17β-ol,
1′-mesyl-17α-methyl-11-methylene-1′H-androst-4-eno[3,2-c]pyrazol-17β-ol,
11β-fluoro-1′-mesyl-17α-methyl-1′H-androsteno[3,2-c]pyrazol-17β-ol,
1′-mesyl-17α-methyl-7α-vinyl-1′H-androst-4-eno[3,2-c]pyrazol-17β-ol,
1′-mesyl-4α,17α-dimethyl-1′H-5α-androstano[3,2-c]pyrazol-17β-ol,
2′-mesyl-4,17α-dimethyl-2′H-triazolo[4′,5′:2,3]androst-4-en-17β-ol,
2′-mesyl-17α-methyl-2′H-triazolo[4′,5′:2,3]androst-4-en-17β-ol,
2′-mesyl-17α-methyl-2′H-triazolo[4′,5′:2,3]androsta-4,15-dien-17β-ol,
2′-mesyl-4,17α-dimethyl-2′H-triazolo[4′,5′:2,3]androsta-4,15-dien-17β-ol,
6,6-ethylene-2′-mesyl-17α-methyl-2′H-triazolo[4′,5′:2,3]androst-4-en-17β-ol,
2′-mesyl-17α-methyl-7α-vinyl-2′H-triazolo[4′,5′:2,3]androst-4-en-17β-ol,
2′-mesyl-7α,17α-dimethyl-2′H-triazolo[4′,5′:2,3]androst-4-en-17β-ol,
2′-mesyl-17α-methyl-2′H-triazolo[4′,5′:2,3]androsta-4,6-dien-17β-ol,
2′-mesyl-17α-methyl-11-methylene-2′H-triazolo[4′,5′:2,3]androst-4-en-17β-ol, 11β-fluoro-2′-mesyl-17α-methyl-2′H-triazolo[4′,5′:2,3]androst-4-en-17β-ol.

Steroido [3,2-c]pyrazoles of the stanozolol type (stanozolol=17α-methyl-5α-androstano[3,2-c]pyrazol-17β-ol) have been disclosed in EP 0 207 375 A1. These compounds are androstanes of the 5α-H or 4-ene series exhibiting a pyrazole ring condensed to the A ring of the steroid and substituted at the N-1. These compounds have antiandrogenic properties and are peripherally selectively effective. EP 0 207 375 A1 indicates 17α-ethynyl-1'-mesyl-1'H-5α-androstano[3,2-c]pyrazol-17β-ol and 17α-ethynyl-1'-mesyl-4-methyl-1'H-androst-4-eno[3,2-c]pyrazol-17β-ol as the especially preferred compounds.

These two compounds, in the classical antiandrogen test on orchiectomized, testosterone propionate-substituted rats (dose: 0.1 mg/animal/day) show, after a seven day treatment (s.c.) with 3 mg/animal/day of the antiandrogen, merely about 30% of the antiandrogenic potency of cyproterone acetate (17α-acetoxy-6-chloro-1α,2α-methylene-4,6-pregnadiene-3,20-dione) which constitutes the standard antiandrogen (Friedmund Neumann, Rudolf Wiechert, "Die Geschichte von Cyproteronacetat, Ungewoehnliche Wege bei der Entwicklung eines Arzneimittels" [The History of Cyproterone Acetate, the Development of a Medicine Along Unusual Routes], MPS Medizinisch-Pharmazeutische Studiengesellschaft e.V. [Association for Medical-Pharmaceutical Studies] Mainz, Mainz 1984).

The strongest antiandrogen described in EP 0 207 375 A1 with an antiandrogenic activity comparable to cyproterone acetate is 4,17α-dimethyl-1'-mesyl-1'H-androst-4-eno[3,2-c]pyrazol-17β-ol, but this compound raises the testosterone level in the serum on account of its central effect (counter regulation by feedback) and thus has no peripheral selectivity.

In order to test peripheral selectivity, the testosterone levels are measured in rats 24 hours after administration of 10 mg s.c. of the compound: lack of counter regulation is evaluated as peripheral selectivity.

It is, therefore, an object of the present invention to provide compounds exhibiting approximately the efficacy of cyproterone acetate but without affecting, as does the latter compound, the hypothalamushypophysis system, i.e. compounds are to be found which are effective only peripherally selectively, which do not bring about the release of androgenically active compounds by a centrally controlled counter regulation.

It has now been discovered that the compounds of general Formula I surprisingly represent antiandrogens having the desired peripheral selectivity, and that they possess almost the efficacy of cyproterone acetate.

Table 1 shows a comparison of the compounds of this invention, (A) 1'-mesyl-17α-methyl-1'H-androsta-4,15-dieno[3,2-c]pyrazol-17β-ol, (B) 6,6-ethylene-1'-mesyl-17α-methyl-1'H-androst-4-eno[3,2-c]pyrazol-17β-ol, (C) 7α,17α-dimethyl-1'-mesyl-1'H-androst-4-eno[3,2-c]pyrazol-17β-ol, (D) 2'-mesyl-17α-methyl-2'H-triazolo[4',5':2,3]androsta-4,15-dien-17β-ol, with compound (E) 4,17α-dimethyl-1'-mesyl-1'H-androst-4-eno[3,2-c]pyrazol-17β-ol described in EP 0 207 375.

TABLE 1

| Compound | Antiandrogen Test (3 mg s.c.) % Inhibition of Prostate Weight | Counter Regulation |
|---|---|---|
| A | 80 (97)* | No |
| B | 73 (86)* | No |
| C | 53 (87)* | No |
| D | 97 (95)* | No |
| E | 88 (100)* | Yes |

*Comparison Cyproterone Acetate

The novel compounds of general Formula I differ from the known compounds if (a) X is a CH group, by an additional 15,16-double bond, by an additional 15α(β),16α(β)-methylene bridge and/or by an additional 6,6-methylene or 6,6-ethylene group and/or by an additional $C_1$- to $C_4$-alkyl group in the 7α or β-position of the steroid skeleton, or (b) X is a nitrogen atom, at least by this nitrogen atom.

The present invention also concerns a process for the preparation of the compounds of general Formula I.

In this process, if X in the compound of Formula I (a) is to be a CH group, a steroido[3,2-c]-1'H-pyrazole of general Formula IIa

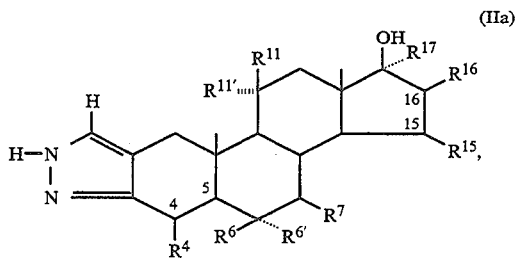

wherein

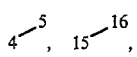

$R^4$, $R^6$, $R^{6'}$, $R^7$, $R^{11}$, $R^{11'}$, $R^{15}$, $R^{16}$ and $R^{17}$ have the meanings indicated in Formula I (X=CH), is sulfonylated or, respectively, acylated with a compound of Formula IIIa or Formula IIIb $$R—SO_2—X^a \quad \text{(IIIa)}$$

or $$R—C(O)—X^b \quad \text{(IIIb)}$$

wherein $X^a$ and $X^b$ mean a chlorine or bromine atom, or alternatively $X^a$ means the residue O—$SO_2$—R or $X^b$ means the residue O—C(O)—R, and R has the meanings given in Formula I, to a compound of general Formula I (X=CH); or (b) X is to be a nitrogen atom, an alkylsulfonylhydrazone of general Formula IIb

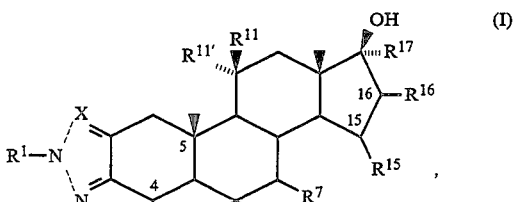

wherein

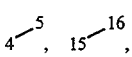

$R^4$, $R^6$, $R^{6'}$, $R^7$, $R^{11}$, $R^{11'}$, $R^{15}$, $R^{16}$ and $R^{17}$ have the meanings indicated in Formula I (X=N), is cyclized to a compound of general Formula I (X=N).

The sulfonylation of the compounds of general Formula IIa takes place according to customary methods described, for example, in EP 0 207 375 A1 and disclosed in the examples of this invention.

Methods known to a person skilled in the art are likewise employed for the acylation.

The ring closure of the alkylsulfonylhydrazones of general Formula IIb to the triazoles of general Formula I (X=N) is obtained, for example, by reacting IIb with methanesulfonic acid chloride in pyridine.

The invention furthermore concerns pharmaceutical preparations containing at least one compound of general Formula I as well as a pharmaceutically compatible vehicle.

In order to determine the respective antiandrogenically effective amount of a compound of general Formula I, the methods described in the foregoing can be utilized.

Based on their high antiandrogenically effective strength, with a simultaneously peripherally selective effect, the compounds of this invention can be primarily employed for the production of medicinal agents suitable for the therapy of benign prostate hyperplasia and androgen-dependent prostate carcinoma. However, they can also be utilized for the treatment of other androgen-dependent disorders and diseases.

The pharmaceutical preparations can be provided for oral, parenteral, transdermal, rectal or vaginal administration and can be prepared in a solid or liquid dosage form, such as, for example, as capsules, tablets, suppositories, solutions, suspensions and emulsions.

A daily dose of 10–1,000 mg/day, preferably 50–500 mg/day and most preferably 50–200 mg/day, of a compound of general Formula I is administered for the treatment of benign prostate hyperplasia, of androgen-dependent prostate carcinoma, as well as other androgen-dependent disorders and diseases, e.g., in mammals including humans. Typically, the dosage is 1–20 mg/kg/day.

Non-limiting examples of other appropriate androgen-dependent disorders and diseases include acne, polycystic ovaries, alopezia, androgen-dependent tumors other than prostate cancer (i.e., tumors which contain androgen receptors). Androgen dependency is readily ascertainable by those of skill in the art, e.g., androgen-dependent prostate cancers are those which are dependent on or sensitive in their growth to androgens.

The compounds of this invention are typically administered analogously to cyproterone acetate.

Biologically equivalent amounts can be determined in a simple way in comparative tests in accordance with the methods set forth above.

For preparing the pharmaceutical products, the active agents of general Formula I are further processed with the use of conventional inert and pharmaceutically compatible vehicles (carrier substances) according to procedures conventional in galenic pharmacy.

The steroido[3,2-c]-1'H-pyrazoles of general Formula IIa needed for preparing the compounds of general Formula I

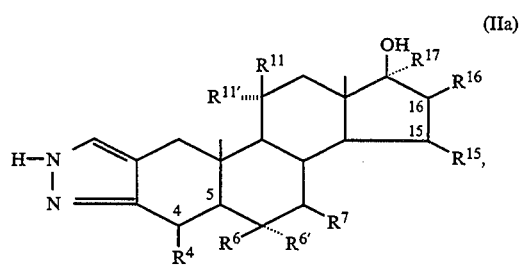

wherein

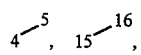

$R^4$, $R^6$, $R^{6'}$, $R^7$, $R^{11}$, $R^{11'}$, $R^{15}$, $R^{16}$ and $R^{17}$ have the meanings indicated in Formula I (X=CH), are obtained by condensation of the respectively correspondingly substituted 2-hydroxymethylene-3-keto steroids of general Formula IV

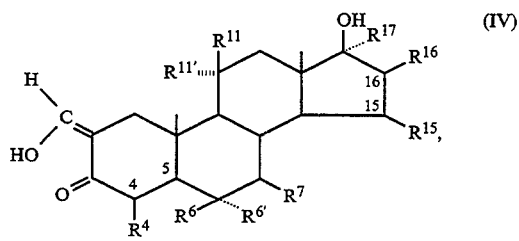

with hydrazine. The reaction conditions can be derived from Synthesis Example 33.

The 2-hydroxymethylene-3-keto steroids of general Formula IV also serve as the starting compounds for the preparation of the alkylsulfonylhydrazones of general Formula IIb required for the cyclization reaction (b). Reaction of the 2-hydroxymethylenes of Formula IV with nitrous acid leads to the corresponding 2-oximes which are converted, in an acidic medium, with methanesylfonylhydrazide into the alkylsulfonylhydrazones IIb.

In order to obtain the compounds of general Formula IV, various synthesis routes are needed, depending on the finally desired meanings (thus being also present already in Formula IV) of the substituents $R^4$, $R^6$, $R^{6'}$, $R^7$, $R^{11}$, $R^{11'}$, $R^{15}$, $R^{16}$ and $R^{17}$, as well as

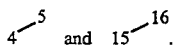

These are all readily determinable with the guidance of this application, especially as follows.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 21 433.8, are hereby incorporated by reference.

(A) Preparation of the 15-ene Compounds Unsubstituted at C-4 ($R^4$=H, $C_{15}$-$C_{16}$=Double Bond)

15α-Hydroxy-4-androstene-3,17-dione 1 (DE-A 3,404,862) is converted via the 15α-acetate 2 into the 3-dienol methyl ether 3. Nucleophilic addition of alkyl lithium $R^{17}$-Li or alkyl magnesium halide $R^{17}$-MgHal with Hal=Cl, Br, I ($R^{17}$ having the meanings indicated in general Formula I), lithium ethynyl, lithium chloroethynyl and, respectively, lithium propynyl results, with additional elimination of the 15α-acetoxy group, in the 15-ene-17α-alkyl or 17α-alkynyl carbinols 4 which, in an acidic medium, pass over into the 3-keto-4,15-diene steroids 5. Reaction of 5 with, for example, ethyl formate in the presence of a strong base, such as, for example, sodium hydride or sodium methylate, leads to the required 2-hydroxymethylene-3-keto steroid of general Formula IVa.

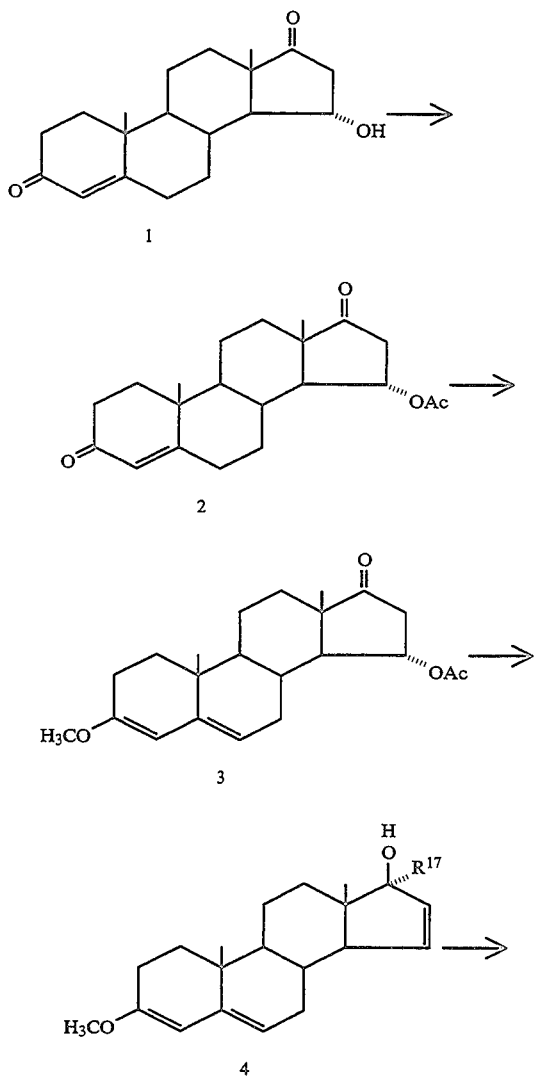

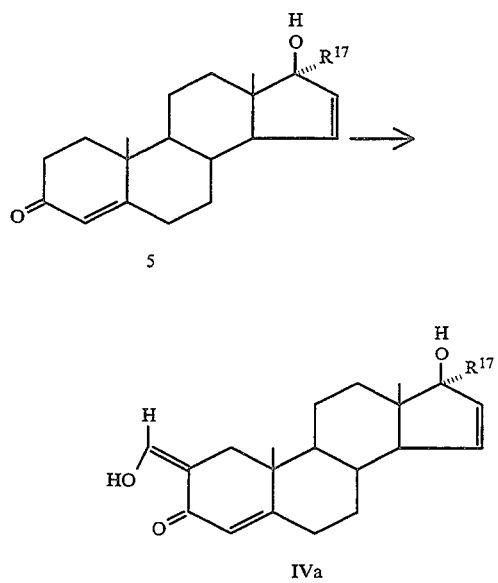

(B) Preparation of the 4,17-Dimethyl-15-ene Steroids ($R^4$=$CH_3$, $R^{17}$=$CH_3$)

17β-Hydroxy-17α-methyl-4,15-androstadien-3-one (compound 5 in the above scheme wherein $R^{17}$=$CH_3$) is converted, according to Petrow et al. (J. Chem. Soc. 1962: 1091), by way of the 4-phenylthiomethyl steroid 6 and subsequent Raney nickel treatment into the 4-methyl compound 7. The reaction 7 to the required 2-hydroxymethylene-3-keto compound of general Formula IVb takes place as described above in (A).

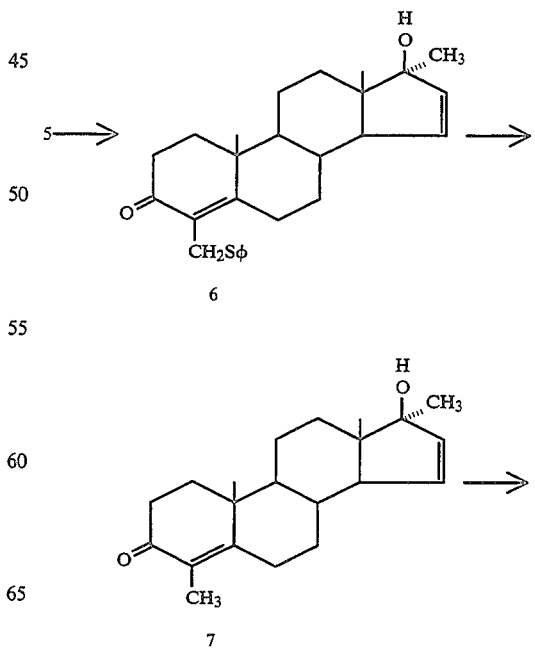

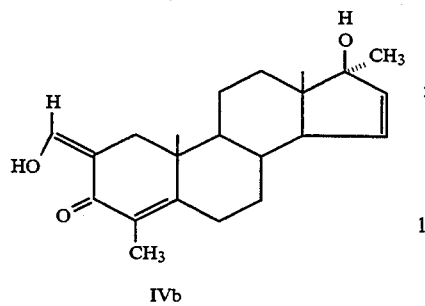

IVb (C) Preparation of the 4,15-Diene-4-methyl-17α-alkynyl Carbinols

In the presence of a 17-alkynyl group, a 4-methyl group cannot be introduced at the 4-ene-3-keto system according to Petrow et al. since in this case the 17α-ethynyl group is likewise attacked. Consequently, the starting compound 1 in (A) is converted analogously to (B) in accordance with Petrow et al. by way of 8 into the 4-methyl compound 9. After acetylation of the 15-hydroxy group to 10 and formation of the 3-dienol methyl ether 11, the reaction yields the 15-ene-17α-alkynyl carbinol 12 with alkynyl lithium $R^{17'}$-Li ($R^{17'}$=ethynyl or propynyl) with additional splitting off of the 15-ester group. After cleavage of the 3-dienol ether to 13 in the way described above, the 2-hydroxymethylene group is introduced analogously to (A), obtaining the required starting compound IVc.

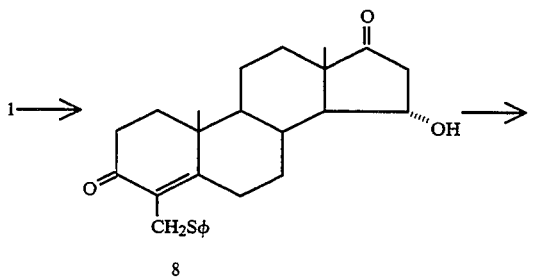

8

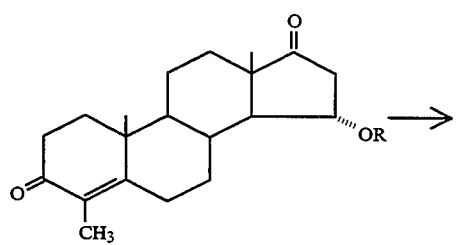

9: R = H
10: R = C(O)CH$_3$

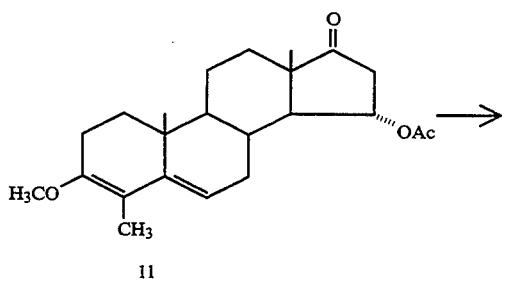

11

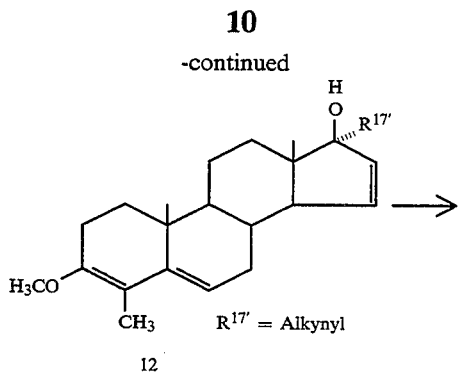

$R^{17'}$ = Alkynyl

12

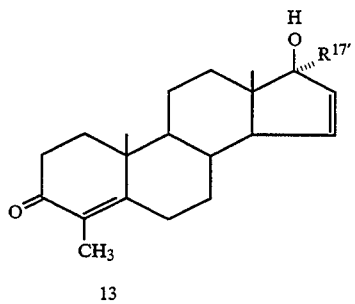

13

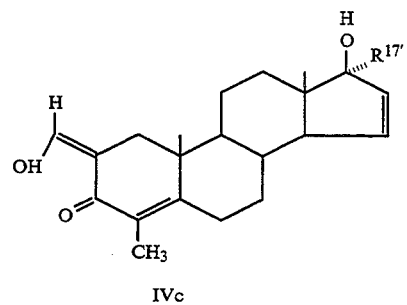

IVc (D) Synthesis of the Steroid Pyrazoles with $C_{15}$–$C_{16}$ Single Bond

This synthesis is accomplished from the 17α-alkyl or 17α-ethynyl testosterone derivatives (i.e. $R^{15}$=H or alkyl), correspondingly substituted on the number 4, 6 and/or 7 carbon atoms, in an analogous reaction sequence as indicated in the reaction schemes under (A) through (C).

The examples set forth below serve for a more detailed description of the invention.

PREPARATION OF THE STARTING COMPOUNDS

Example 1

17β-Hydroxy-17α-methylandrosta-4,15-dien-3-one (a) 15α-Acetoxy-4-androstene-3,17-dione 168 g of 15α-hydroxy-4-androstene-3,17-dione in 250 ml of pyridine and 125 ml of acetic anhydride are heated on a steam bath. After 90 minutes, the reaction mixture is stirred into ice/water. The thus-precipitated product is suctioned off, taken up in methylene chloride, washed with water, and dried over sodium sulfate. After recrystallization from ethyl acetate, 120 g of 15α-acetoxy-4-androstene-3,17-dione is obtained, mp 145° C.

(b) 15α-Acetoxy-3-methoxyandrosta-3,5-dien-17-one 10.0 g of 15α-acetoxy-4-androstene-3,17-dione is stirred under reflux with 60 ml of dimethoxypropane and 1.0 g of pyridinium-4-toluenesulfonate. After 5 hours, 1 ml of pyridine is added, the mixture is diluted with ethyl acetate, washed neutral with water, and dried. The crude product is recrystallized from hexane-/acetone. Yield: 9.6 g of 15α-acetoxy-3-methoxyandrosta-3,5-dien-17-one, mp 209° C.

(c) 3-Methoxy-17α-methylandrosta-3,5,15-trien-17β-ol

At 0° C., 80 ml of a 1.6-molar ethereal methyllithium solution is added dropwise under argon to 13.2 g of 15α-acetoxy-3-methoxyandrosta-3,5-dien-17-one in 500 ml of tetrahydrofuran. After 45 minutes, the mixture is gently combined with saturated ammonium chloride solution, diluted with ethyl acetate, washed with water, dried, and concentrated under vacuum. After chromatographing of the crude product on silica gel with a hexane-ethyl acetate gradient, 11.9 g of 3-methoxy-17α-methylandrosta-3,5,15-trien-17β-ol is obtained, mp 146.8° C. (from acetone/hexane).

(d) 17β-Hydroxy-17α-methylandrosta-4,15-dien-3-one

At room temperature, 12 ml of concentrated hydrochlorid acid is added dropwise to 14.9 g of 3-methoxy-17α-methylandrosta-3,5,15-trien-17β-ol in 360 ml of methanol and 37 ml of water. After 3 hours, the reaction mixture is stirred into ice/water. The thus-precipitated product is suctioned off, washed with water, dried, and concentrated under vacuum. The crude product is chromatographed on silica gel with a hexane-ethyl acetate gradient. Yield: 5.8 g of 17β-hydroxy-17α-methylandrosta-4,15-dien-3-one, mp 170.3° C. (from acetone/hexane).

Example 2

17α-Ethynyl-17β-hydroxyandrosta-4,15-dien-3-one

Acetylene is introduced at 0° C. for 45 minutes into 200 ml of butyllithium solution (1.6 molar in hexane) in 600 ml of tetrahydrofuran. Then 20.0 g of 15α-acetoxy-3-methoxyandrosta-3,5-dien-17-one in 400 ml of tetrahydrofuran is added thereto. After 2 hours, the mixture is gently combined with saturated ammonium chloride solution, diluted with ethyl acetate, washed with water, dried, and concentrated under vacuum. At room temperature, 14 ml of concentrated hydrochloric acid is added dropwise to the crude product in 400 ml of methanol and 50 ml of water. After 1.5 hours, the reaction mixture is stirred into ice/water. The thus-precipitated product is suctioned off, washed with water, dissolved in ethyl acetate, dried, and concentrated under vacuum. The crude product is chromatographed on silica gel with a hexane-ethyl acetate gradient, thus obtaining 9.5 g of 17α-ethynyl-17β-hydroxyandrosta-4,15-dien-3-one, mp 206.4° C. (from acetone/hexane).

Example 3

17α-Chloroethynyl-17β-hydroxyandrosta-4,15-dien-3-one

At 0° C., 80 ml of methyllithium solution (1.6 molar in diethyl ether) is added dropwise to 6 ml of 1,2-dichloroethylene in 100 ml of diethyl ether. After 30 minutes, 6.3 g of 15α-acetoxy-3-methoxyandrosta-3,5-dien-17-one in 100 ml of tetrahydrofuran is added thereto. The reaction mixture is combined, after 15 minutes, with saturated ammonium chloride solution, diluted with ethyl acetate, washed with water, dried, and concentrated under vacuum. At room temperature, 4 ml of concentrated hydrochloric acid is added dropwise to the crude product in 130 ml of methanol and 15 ml of water. After 30 minutes, the reaction mixture is stirred into ice/water, the precipitated product is suctioned off, washed with water, dissolved in ethyl acetate, dried, and concentrated under vacuum. The crude product is chromatographed on silica gel with a hexane-ethyl acetate gradient, thus obtaining 2.6 g of 17α-chloroethynyl-17β-hydroxyandrosta-4,15-dien-3-one as a foam.

Example 4

17α-Bromoethynyl-17β-hydroxyandrosta-4,15-dien-3-one

At room temperature, 4.0 g of 17α-ethynyl-17β-hydroxyandrosta-4,15-dien-3-one in 80 ml of acetone and 10 ml of water is combined with 2.8 g of N-bromosuccinimide and 300 mg of silver nitrate. After 30 minutes, the reaction mixture is introduced into ice/water which contains sodium sulfite. The precipitated product is suctioned off, washed with water, dissolved in ethyl acetate, dried, and concentrated under vacuum, yielding 4.1 g of 17α-bromoethynyl-17β-hydroxyandrosta-4,15-dien-3-one as a foam.

Example 5

17β-Hydroxy-17α-propyn-1-ylandrosta-4,15-dien-3-one

At 0° C., propyne is introduced for 30 minutes into 150 ml of butyllithium solution (1.6 molar in hexane) in 400 ml of tetrahydrofuran. Then 15 g of 15α-acetoxy-3-methoxyandrosta-3,5-dien-17-one in 300 ml of tetrahydrofuran is added dropwise thereto, the mixture is allowed to react for 1 hour and combined with saturated ammonium chloride solution. The mixture is diluted with ethyl acetate, washed with water, dried, and concentrated under vacuum. The crude product is combined dropwise with 10 ml of concentrated hydrochloric acid in a mixture of 300 ml of methanol and 20 ml of water at room temperature. After 1 hour, the reaction mixture is introduced into ice/water, the precipitated product is suctioned off, washed with water, dissolved in ethyl acetate, dried, and concentrated under vacuum. After chromatography of the crude product on silica gel with a hexane-ethyl acetate gradient, 6.3 g of 17β-hydroxy-17α-propyn-1-ylandrosta-4,15-dien-3-one is obtained as a foam.

Example 6

17β-Hydroxy-4,17α-dimethylandrosta-4,15-dien-3-one (a) 17β-Hydroxy-17α-methyl-4-(phenylthiomethyl)androsta-4,15-dien-3-one Under argon, 9.2 g of 17β-hydroxy-17α-methylandrosta-4,15-dien-3-one in 80 ml of triethanolamine is allowed to react at 110° C. with 2.1 ml of thiophenol and 2.1 ml of aqueous formaldehyde solution (37%). After 5 hours and another 18 hours, respectively 2.1 ml of thiophenol and 2.1 ml of formaldehyde solution are added. In total, the reaction mixture is stirred for 32 hours and subsequently introduced into ice/water. The precipitated product is suctioned off, washed with water, taken up in methylene chloride, dried, and concentrated under vacuum. After chromatographing the crude product on silica gel with a hexane-ethyl acetate gradient, 7.9 g of 17β-hydroxy-17α-methyl-4-(phenylthiomethyl)androsta-4,15-dien-3-one is obtained, mp 146.8° C. (from acetone/hexane).

(b) 17β-Hydroxy-4,17α-dimethylandrosta-4,15-dien-3-one

About 10 g of Raney nickel in 200 ml of acetone is combined with 6.8 g of 17β-hydroxy-17α-methyl-4-(phenylthiomethyl)androsta-4,15-dien-3-one in 200 ml of acetone, and the mixture is stirred under argon at room temperature. After 30 hours, the mixture is decanted from the Raney nickel, the Raney nickel is washed repeatedly with acetone, the acetone solutions are combined, filtered over "Celite", and the filtrate is concentrated under vacuum. The crude product is recrystallized from acetone/hexane. Yield: 3.4 g of 17β-hydroxy-4,17α-dimethylandrosta-4,15-dien-3-one, mp 184° C. (from acetone/hexane).

Example 7

17α-Ethynyl-17β-hydroxy-4-methylandrosta-4,15-dien-3-one (a) 15α-Hydroxy-4-(phenylthiomethyl)androst-4-ene-3,17-dione 15 g of 15α-hydroxyandrost-4-ene-3,17-dione is reacted analogously to Example 6(a) with thiophenol and formaldehyde in triethanolamine. Chromatography of the crude product on silica gel with a hexane-ethyl acetate gradient yields 11 g of 15α-hydroxy-4-(phenylthiomethyl)androst-4-ene-3,17-dione as a foam.

(b) 15α-Hydroxy-4-methylandrost-4-ene-3,17-dione

Analogously to Example 6(b), 10.0 g of 15α-hydroxy-4-(phenylthiomethyl)androst-4-ene-3,17-dione is treated with Raney nickel, thus isolating 4.8 g of 15α-hydroxy-4-methylandrost-4-ene-3,17-dione as a foam.

(c) 15α-Acetoxy-4-methylandrost-4-ene-3,17-dione 4.2 g of 15α-hydroxy-4-methylandrost-4-ene-3,17-dione is acetylated analogously to Example 1(a). Chromatography of the crude product on silica gel with a hexane-ethyl acetate gradient yields 3.9 g of 15α-acetoxy-4-methylandrost-4-ene-3,17-dione.

(d) 15α-Acetoxy-3-methoxy-4-methylandrosta-3,5-dien-17-one 5.0 g of 15α-acetoxy-4-methylandrost-4-ene-3,17-dione is stirred at 80° C. in 40 ml of 2,2-dimethoxypropane with 500 mg of pyridinium 4-toluenesulfonate. After 6 hours, 1 ml of triethylamine is added thereto; the mixture is diluted with ethyl acetate, washed with water, dried, and concentrated under vacuum. The crude product is chromatographed on silica gel containing 2% triethylamine with a hexane-ethyl acetate gradient, thus obtaining 3.8 g of 15α-acetoxy-3-methoxy-4-methylandrosta-3,5-dien-17-one as an oil.

(c) 17α-Ethynyl-17β-hydroxy-4-methylandrosta-4,15-dien-3-one 3.5 g of 15α-acetoxy-3-methoxy-4-methylandrosta-3,5-dien-17-one is reacted with acetylene analogously to Example 5. The resultant 17α-ethynyl-3-methoxy-4-methylandrosta-3,5,15-trien-17β-ol is allowed to react, as described in Example 5, with concentrated hydrochloric acid in a mixture of methanol/water. After the crude product has been chromatographed on silica gel with a hexane-ethyl acetate gradient, 1.3 g of 17α-ethynyl-17β-hydroxy-4-methylandrosta-4,15-dien-3-one is obtained as a foam.

Example 8

17β-Hydroxy-17α-methyl-6-methyleneandrosta-4,15-dien-3-one 500 mg of 17β-hydroxy-17α-methylandrosta-4,15-dien-3-one in 8.3 ml of tetrahydrofuran is stirred at 60° C. under argon with 348 mg of paraformaldehyde and 2.2 g of N-methylanilinium trifluoroacetate. After 3.5 hours, the mixture is diluted with ethyl acetate, washed with water, dried over sodium sulfate, and concentrated under vacuum. After the crude product has been chromatographed on silica gel with a pentane-diethyl ether gradient, 226 mg of 17β-hydroxy-17α-methyl-6-methyleneandrosta-4,15-dien-3-one is obtained, mp 162° C. (from isopropyl ether).

Example 9

17β-Hydroxy-4,17α-dimethyl-6-methyleneandrost-4-en-3-one (a) 17β-Hydroxy-17α-methyl-6-methylene-4-(phenylthiomethyl)androst-4-en-3-one p Analogously to Example 6(a), 200 mg of 17β-hydroxy-17α-methyl-6-methyleneandrost-4-en-3-one (Tetrahedron 20: 597, 1964) is reacted with thiophenol and formaldehyde in triethanolamine. After chromatography of the crude product on silica gel with a hexane-ethyl acetate gradient, 190 mg of 17β-hydroxy-17α-methyl-6-methylene-4-(phenylthiomethyl)androst-4-en-3-one is obtained as an oil.

(b) 4,17α-Dimethyl-17β-hydroxy-6-methyleneandrost-4-en-3-one 400 mg of 17β-hydroxy-17α-methyl-6-methylene-4-(phenylthiomethyl)androst-4-en-3-one is treated with Raney nickel analogously to Example 6(b), thus obtaining 107 mg of 4,17α-dimethyl-17β-hydroxy-6-methyleneandrost-4-en-3-one, mp 193°–196° C.

Example 10

17β-Hydroxy-4,7α,17α-trimethylandrost-4-en-3-one (a) 17β-Hdyroxy-7α,17α-dimethyl-4-(phenylthiomethyl)androst-4-en-3-one 1.3 g of 17β-hydroxy-7α,17α-dimethylandrost-4-en-3-one (Steroids 1: 299, 1963) is reacted analogously to Example 6(a) with thiophenol and formaldehyde in triethanolamine, thus isolating 2 g of 17β-hydroxy-7α,17α-dimethyl-4-(phenylthiomethyl)androst-4-en-3-one as a crude product.

(b) 17β-Hydroxy-4,7α,17α-trimethylandrost-4-en-3-one

Analogously to Example 6(b), 2.0 g of 17β-hydroxy-7α,17α-dimethyl-4-(phenylthiomethyl)androst-4-en-3-one is treated with Raney nickel. After the crude product has been chromatographed on silica gel with a pentane-diethyl ether gradient, 765 mg of 17β-hydroxy-4,7α,17α-trimethylandrost-4-en-3-one is obtained, mp 126° C. (from isopropyl ether).

Example 11

17β-Hydroxy-17α-methyl-11-methyleneandrost-4-en-3-one (a) 3,3;17,17-Bisethylenedioxyandrost-5-en-11α-ol 50 g of 11α-hydroxyandrost-4-ene-3,17-dione [J. Org. Chem. 19: 40 (1954)] in 370 ml of methylene chloride, 315 ml of ethylene glycol and 105 ml of trimethyl orthoformate is stirred with 530 mg of p-toluenesulfonic acid at 60° C. After 6 hours, 10 ml of pyridine is added, the mixture is concentrated under vacuum, and the residue is introduced into ice/water. The precipitated product is suctioned off, washed with water, dissolved in methylene chloride, dried, and concentrated under vacuum. After crystallization from ethyl acetate, 49 g of 3,3;17,17-bisethylenedioxyandrost-5-en-11α-ol is obtained, mp 211°–216° C. (from acetone/hexane).

(b) 3,3;17,17-Bisethylenedioxyandrost-5-en-11-one

Under ice/water cooling, 66.2 g of pyridinium dichromate is added to 48 g of 3,3;17,17-bisethylenedioxyandrost-5-en-11α-ol in 290 ml of dimethylformamide. The mixture is then stirred at room temperature. After 20 hours, the mixture is introduced into 2 liters of ethyl acetate and filtered over kieselguhr. The ethyl acetate phase is washed with water, dried, and concentrated under vacuum, thus obtaining 39 g of 3,3;17,17-bisethylenedioxyandrost-5-en-11-one, mp 180°–182° C. (from acetone/hexane).

(c) 3,3;17,17-Bisethylenedioxy-11α-methylandrost-5-en-11β-ol

Under argon and ice/water cooling, 10 g of 3,3;17,17-bisethylenedioxyandrost-5-en-11-one in 130 ml of tetrahydrofuran is added to 98 ml of an ethereal methyllithium solution (1.6 molar) in 130 ml of tetrahydrofuran. After 1 hour, saturated ammonium chloride solution is gradually added dropwise, the mixture is diluted with ethyl acetate, washed with water, dried, and concentrated under vacuum. After crystallization from acetone/hexane, 7 g of 3,3;17,17-bisethylenedioxy-11α-methylandrost-5-en-11β-ol is obtained, mp 187°–189° C. (from acetone/hexane).

(d) 11β-Hydroxy-11α-methylandrost-4-ene-3,17-dione 2.1 g of 3,3;17,17-bisethylenedioxy-11α-methylandrost-5-en-11β-ol in 40 ml of acetone is combined with 0.8 ml of 2N hydrochloric acid at room temperature. After 6 hours, the solution is introduced into ice/water. The precipitated product is suctioned off, washed with water, dried, and concentrated under vacuum. After chromatography of the crude product on silica gel with a methylene chloride-ethyl acetate gradient and crystallization from acetone/hexane, 1.1 g of 11β-hydroxy-11α-methylandrost-4-ene-3,17-dione is obtained, mp 150°–151° C. (from acetone/hexane).

(e) 11-Methyleneandrost-4-ene-3,17-dione 9 g of 11β-hydroxy-11α-methylandrost-4-ene-3,17-dione is allowed to react with 100 ml of concentrated formic acid at 50° C. After 6 hours, the solution is stirred into ice/water that contains sodium hydroxide. The precipitated product is suctioned off, washed with water, dissolved in ethyl acetate, dried, and concentrated under vacuum. The crude product is chromatographed on silica gel with a methylene chloride-ethyl acetate gradient, thus obtaining 5 g of 11-methyleneandrost-4-ene-3,17-dione, mp 157°–160° C. (from acetone/hexane).

(f) 3,3-Ethylenedithio-11-methyleneandrost-4-en-17-one

At room temperature, 0.2 ml of boron trifluoride etherate and 0.6 ml of 1,2-ethanedithiol are added to a suspension of 1 g of 11-methyleneandrost-4-ene-3,17-dione in 5 ml of methanol. After 22 hours, the reaction mixture is introduced into ice/water, the precipitated product is suctioned off and washed with cold methanol. Chromatography of the crude product on silica gel with a hexane-ethyl acetate gradient yields 960 mg of 3,3-ethylenedithio-11-methyleneandrost-4-en-17-one, mp 215°–216° C. (from acetone/hexane).

(g) 3,3-Ethylenedithio-17α-methyl-11-methyleneandrost-4-en-17β-ol

At room temperature, 5.4 ml of methyl magnesium bromide solution (3 molar in diethyl ether) is added under argon to 1 g of 3,3-ethylenedithio-11-methyleneandrost-4-en-17-one in 15 ml of tetrahydrofuran. After 4 hours, saturated ammonium chloride solution is added, the mixture is diluted with ethyl acetate, washed with water, and dried. The crude product is chromatographed on silica gel with a hexaneacetone gradient, thus obtaining 820 mg of 3,3-ethylenedithio-17α-methyl-11-methyleneandrost-4-en-17β-ol, mp 174°–175° C. (from acetone/hexane).

(h) 17β-Hydroxy-17α-methyl-11-methyleneandrost-4-en-3-one

At room temperature, 800 mg of [bis(trifluoroacetoxy)iodo]benzene is added to 500 mg of 3,3-ethylenedithio-17α-methyl-11-methyleneandrost-4-en-17β-ol in 18 ml of methanol and 2 ml of water. After 10 minutes, the reaction mixture is stirred into ice/water. The precipitated product is suctioned off, washed with water, dissolved in ethyl acetate, dried, and concentrated under vacuum. Chromatography of the crude product on silica gel with a hexane-acetone gradient yields 320 mg of 17β-hydroxy-17α-methyl-11-methyleneandrost-4-en-3-one, mp 155°–157° C. (from acetone/hexane).

Example 12

11β-Fluoro-17β-hydroxy-17α-methylandrost-4-en-3-one (a) 11β-Fluoro-3-methoxyandrosta-3,5-dien-17-one 10.0 g of 11β-fluoroandrost-4-ene-3,17-dione [U.S. Pat. No. 3,966,713 (1976)] is stirred under reflux with 60 ml of dimethoxypropane and 1.0 g of pyridinium-4-toluenesulfonate. After 8 hours, 1 ml of pyridine is added, the mixture is diluted with ethyl acetate, washed neutral with water, and dried. The crude product is chromatographed on silica gel with an acetone-hexane gradient. Yield: 7.8 g of 11β-fluoro-3-methoxyandrosta-3,5-dien-17-one as a foam.

(b) 11β-Fluoro-3-methoxy-17α-methylandrosta-3,5-dien-17β-ol

At 0° C., 8 ml of a 1.6-molar ethereal methyllithium solution is added dropwise under argon to 1.4 g of 11β-fluoro-3-methoxyandrosta-3,5-dien-17-one in 50 ml of tetrahydrofuran. After 45 minutes, the mixture is gently combined with saturated ammonium chloride solution, diluted with ethyl acetate, washed with water, dried, and concentrated under vacuum. After chromatography of the crude product on silica gel with a hexane-ethyl acetate gradient, 900 mg of 11β-fluoro-3-methoxy-17α-methylandrosta-3,5-dien-17β-ol is obtained as a foam.

(c) 11β-Fluoro-17β-hydroxy-17α-methylandrost-4-en-3-one

At room temperature, 1.2 ml of concentrated hydrochloric acid is added dropwise to 1.5 g of 11β-fluoro-3-methoxy-17α-methylandrosta-3,5-dien-17β-ol in 35 ml of methanol and 3.5 ml of water. After 1 hour, the reaction mixture is stirred into ice/water. The precipitated product is suctioned off, washed with water, dried, and concentrated under vacuum. The crude product is chromatographed on silica gel with a hexaneethyl acetate gradient. Yield: 1.1 g of 11β-fluoro-17β-hydroxy-17α-methylandrost-4-en-3-one as a foam.

Example 13

17β-Hydroxy-17α-methyl-7α-vinylandrost-4-en-3-one (a) 17β-Acetoxy-17α-methyl-3-oxoandrost-4-ene-7α-carbonitrile At room temperature, 17.1 g of 17β-acetoxy-17α-methylandrosta-4,6-dien-3-one [U.S. Pat. No. 3,033,752 (1962)] in 170 ml of toluene is combined with 100 ml of diethyl aluminum cyanide solution (1 mole in toluene). After 24 hours, the reaction mixture is introduced into a potassium sodium tartrate solution, diluted with ethyl acetate, and the mixture is stirred for 1 hour at room temperature, extracted with ethyl acetate, the organic phase is washed with water, dried, and concentrated under vacuum. The resultant crude product is allowed to react in 500 ml of methanol at room temperature with 360 mg of potassium carbonate, the mixture is concentrated under vacuum after 2.5 hours, diluted with ethyl acetate, washed with water, and dried. After the crude product has been chromatographed on silica gel with a methylene chloride (tert-butyl methyl ether) gradient, 13 g of 17β-acetoxy-17α-methyl-3-oxoandrost-4-ene-7α-carbonitrile is obtained, mp 211°–216° C. (from isopropyl ether).

(b) 17β-Acetoxy-3,3-ethylenedithio-17α-methylandrost-4-ene-7α-carbonitrile

At room temperature, 0.2 ml of boron trifluoride etherate and 0.6 ml of 1,2-ethanedithiol are added to a suspension of 1 g of 17β-acetoxy-17α-methyl-3-oxoandrost-4-ene-7α-carbonitrile in 5 ml of methanol. After 3 hours, the reaction mixture is stirred into ice/water, the precipitated product is suctioned off and washed with cold methanol. After the crude product has been chromatographed on silica gel with a pentane-diethyl ether gradient, 1.1 g of 17β-acetoxy-3,3-ethylenedithio-17α-methylandrost-4-ene-7α-carbonitrile is obtained, mp 249°–250° C. (from isopropyl ether).

(c) 3,3-Ethylenedithio-17β-hydroxy-17α-methylandrost-4-ene-7α-carbaldehyde 9.8 g of 17β-acetoxy-3,3-ethylenedithio-17α-methylandrost-4-ene-7α-carbonitrile in 294 ml of toluene is combined at −20° C. under argon with 41.3 ml of diisobutyl aluminum hydride solution (20% in toluene). After 2 hours, the solution is introduced into 600 ml of 10% tartaric acid solution, diluted with ethyl acetate, and stirred for 1 hour at room temperature. After extraction with ethyl acetate, the organic phase is washed with water, dried, and concentrated under vacuum. The crude product is chromatographed on silica gel with a hexane-ethyl acetate gradient. Yield: 4.6 g of 3,3-ethanedithio-17β-hydroxy-17α-methylandrost-4-ene-7α-carbaldehyde as a foam.

(d) 3,3-Ethylenedithio-17α-methyl-7α-vinylandrost-4-en-17β-ol

Under argon and ice/water cooling, 58.5 ml of butyllithium solution (1.3-molar in hexane) is added to a suspension of 34.5 g of methyltriphenylphosphonium bromide in 100 ml of dioxane. The mixture is further stirred at room temperature for 1 hour, and then 4.6 g of 3,3-ethylenedithio-17β-hydroxy-17α-methylandrost-4-ene-7α-carbaldehyde in 60 ml of dioxane is added thereto. After 30 minutes, the reaction mixture is introduced into ice/water, the precipitated product is suctioned off, dissolved in ethyl acetate, washed with water, dried, and concentrated under vacuum. The crude product is chromatographed on silica gel with a hexane-ethyl acetate gradient. Yield: 4 g of 3,3-ethylenedithio-17α-methyl-7α-vinylandrost-4-en-17β-ol, mp 113°–114° C. (from isopropyl ether).

(e) 17β-Hydroxy-17α-methyl-7α-vinylandrost-4-en-3-one 4.6 g of 3,3-ethylenedithio-17α-methyl-7α-vinylandrost-4-en-17β-ol in 115 ml of acetonitrile and 2.3 ml of water is stirred at 70° C. with 2.3 g of sodium bicarbonate and 23.5 ml of methyl iodide. After 6 hours, the mixture is diluted with ethyl acetate, washed with water, dried, and concentrated under vacuum. Chromatography of the crude product on silica gel with a hexane-ethyl acetate gradient yields 3 g of 17β-hydroxy-17α-methyl-7α-vinylandrost-4-en-3-one, mp 116°–117° C. (from isopropyl ether).

PREPARATION OF THE 2-HYDROXYMETHYLENE COMPOUNDS

Example 14

(Z)-17β-Hydroxy-2-hydroxymethylene-17α-methylandrosta-4,15-dien-3-one

At room temperature, 4.6 ml of ethyl formate is added to 4.6 g of 17β-hydroxy-17α-methylandrosta-4,15-dien-3-one in 40 ml of tetrahydrofuran and 70 ml of toluene. Then 3.5 g of sodium hydride (60% paraffin suspension) is added in small portions. After 6 hours, the reaction mixture is gently stirred into ice/water which contains hydrochloric acid, the precipitated product is suctioned off, washed with water, dissolved in methylene chloride, dried, and concentrated under vacuum. After chromatography of the crude product on silica gel with a hexane-ethyl acetate gradient, 2.4 g of (Z)-17β-hydroxy-2-hydroxymethylene-17α-methylandrosta-4,15-dien-3-one is obtained, mp 176° C. (from acetone/hexane).

Example 15

(Z)-17α-Ethynyl-17β-hydroxy-2-hydroxymethyleneandrosta-4,15-dien-3-one

Analogously to Example 14, 9.0 g of 17α-ethynyl-17β-hydroxyandrosta-4,15-dien-3-one is reacted to (Z)-17α-ethynyl-17β-hydroxy-2-hydroxymethyleneandrosta-4,15-dien-3-one. Yield: 6.2 g as a crude product.

Example 16

(Z)-17α-Chloroethynyl-17β-hydroxy-2-hydroxymethyleneandrosta-4,15-dien-3-one 6.2 g of 17α-chloroethynyl-17β-hydroxyandrosta-4,15-dien-3-one is reacted analogously to Example 14 to (Z)-17α-chloroethynyl-17β-hydroxy-2-hydroxymethyleneandrosta-4,15-dien-3-one. Yield: 2.8 g as a foam.

Example 17

(Z)-17α-Bromoethynyl-17β-hydroxy-2-hydroxymethyleneandrosta-4,15-dien-3-one 4.3 g of 17α-bromoethynyl-17β-hydroxyandrosta-4,15-dien-3-one is reacted analogously to Example 14 to (Z)-17α-bromoethynyl-17β-hydroxy-2-hydroxymethyleneandrosta-4,15-dien-3-one. Yield: 2.3 g (oil).

Example 18

(Z)-17β-Hydroxy-2-hydroxymethylene-17α-propyn-1-ylandrosta-4,15-dien-3-one

Analogously to Example 14, 2.9 g of 17β-hydroxy-17α-propyn-1-ylandrosta-4,15-dien-3-one is reacted to (Z)-17β-hydroxy-2-hydroxymethylene-17α-propyn-1-ylandrosta-4,15-dien-3-one. Yield: 1.4 g as a foam.

Example 19

(Z)-17β-Hydroxy-2-hydroxymethylene-4,17α-dimethylandrosta-4,15-dien-3-one 5.0 g of 17β-hydroxy-4,17α-dimethylandrosta-4,15-dien-3-one is reacted analogously to Example 14 to (Z)-17β-hydroxy-2-hydroxymethylene-4,17α-dimethylandrosta-4,15-dien-3-one. Yield: 1.3 g, mp 218° C. (from acetone/hexane).

Example 20

(Z)-17α-Ethynyl-17β-hydroxy-2-hydroxymethylene-4-methylandrosta-4,15-dien-3-one

Analogously to Example 14, 4.6 g of 17α-ethynyl-17β-hydroxy-4-methylandrosta-4,15-dien-3-one is reacted to (Z)-17α-ethynyl-17β-hydroxy-2-hydroxymethylene-4-methylandrosta-4,15-dien-3-one. Yield: 2.1 g as a foam.

Example 21

(Z)-17β-Hydroxy-2-hydroxymethylene-17α-methyl-6-methyleneandrost-4-en-3-one

At room temperature, 2.2 g of sodium methylate is added to 3.0 g of 17β-hydroxy-17α-methyl-6-methyleneandrost-4-en-3-one (Tetrahedron 20: 597, 1964) in 70 ml of pyridine and 10.2 ml of formic acid methyl ester. After 18 hours, the reaction mixture is stirred into ice/water which contains hydrochloric acid. The precipitated product is suctioned off, dissolved in ethyl acetate, washed with water, and dried over sodium sulfate. Chromatography of the crude product on silica gel with a methylene chloride-(tert-butyl methyl ether) gradient yields 2.1 g of (Z)-17β-hydroxy-2-hydroxymethylene-17α-methyl-6-methyleneandrost-4-en-3-one as a foam.

Example 22

(Z)-6,6-Ethylene-17β-hydroxy-2-hydroxymethylene-17α-methylandrost-4-en-3-one 16.0 g of 17βB-acetoxy-6,6-ethylene-17α-methylandrost-4-en-3-one [U.S. Pat. No. 3,499,891 (1970)] is reacted analogously to Example 21. After the crude product has been chromatographed on silica gel with a methylene chloride-(tert-butyl methyl ether) gradient, 15.3 g of (Z)-6,6-ethylene-17β-hydroxy-2-hydroxymethylene-17α-methylandrost-4-en-3-one is obtained as a foam.

Example 23

(Z)-17β-Hydroxy-2-hydroxymethylene-17α-methyl-6-methyleneandrosta-4,15-dien-3-one Analogously to Example 21, 6.8 g of 17β-hydroxy-17α-methyl-6-methyleneandrosta-4,15-dien-3-one is reacted to (Z)-17β-hydroxy-2-hydroxymethylene-17α-methyl-6-methyleneandrosta-4,15-dien-3-one. Yield: 5.3 g as a foam.

Example 24

(Z)-17β-Hydroxy-2-hydroxymethylene-7α,17α-dimethylandrost-4-en-3-one 400 mg of 17β-hydroxy-7α,17α-dimethylandrost-4-en-3-one (Steroids 1: 299, 1963) is reacted analogously to Example 21 to (Z)-17β-hydroxy-2-hydroxymethylene-7α,17α-dimethylandrost-4-en-3-one. Yield: 380 mg as a foam.

Example 25

(Z)-17β-Hydroxy-2-hydroxymethylene-4,17α-dimethyl-6-methyleneandrost-4-en-3-one 2.5 g of 17β-hydroxy-4,17α-dimethyl-6-methyleneandrost-4-en-3-one is reacted analogously to Example 21 to (Z)-17β-hydroxy-2-hydroxymethylene-4,17α-dimethyl-6-methyleneandrost-4-en-3-one. Yield: 2.1 g as a foam.

Example 26

(Z)-17β-Hydroxy-2-hydroxymethylene-4,7α,17α-trimethylandrost-4-en-3-one 700 mg of 17β-hydroxy-4,7α,17α-trimethylandrost-4-en-3-one is reacted analogously to Example 21 to (Z)-17β-hydroxy-2-hydroxymethylene-4,7α,17α-trimethylandrost-4-en-3-one. Yield: 414 mg as a foam.

Example 27

(Z)-17β-Hydroxy-2-hydroxymethylene-7α-methyl-17α-vinylandrost-4-en-3-one 1.3 g of 17β-hydroxy-7α-methyl-17α-vinylandrost-4-en-3-one [U.S. Pat. No. 3,262,949 (1966)] is reacted analogously to Example 14 to (Z)-17β-hydroxy-2-hydroxymethylene-7α-methyl-17α-vinylandrost-4-en-3-one. Yield: 850 mg as a foam.

Example 28

(Z)-17β-Hydroxy-2-hydroxymethylene-17α-methyl-15α,16α-methyleneandrost-4-en-3-one Analogously to Example 14, 314 mg of 17β-hydroxy-17α-methyl-15α,16α-methyleneandrost-4-en-3-one [Chem. Bet. 106: 888 (1973)] is reacted to (Z)-17β-hydroxy-2-hydroxymethylene-17α-methyl-15α,16α-methyleneandrost-4-en-3-one. Yield: 210 mg, mp 199°–200° C. (from acetone/hexane).

Example 29

(Z)-17β-Hydroxy-2-hydroxymethylene-17α-methyl-11-methyleneandrost-4-en-3-one 1.6 g of 17β-hydroxy-17α-methyl-11-methyleneandrost-4-en-3-one is reacted analogously to Example 14 to (Z)-17β-hydroxy-2-hydroxymethylene-17α-methyl-11-methyleneandrost-4-en-3-one. Yield: 960 mg as a foam.

Example 30

(Z)-11β-Fluoro-17β-hydroxy-2-hydroxymethylene-17α-methylandrost-4-en-3-one

Analogously to Example 14, 650 mg of 11β-fluoro-17β-hydroxy-17α-methylandrost-4-en-3-one is reacted to (Z)-11β-fluoro-17β-hydroxy-2-hydroxymethylene-17α-methylandrost-4-en-3-one. Yield: 380 mg as a foam.

Example 31

(Z)-17β-Hydroxy-2-hydroxymethylene-17α-methyl-7α-vinylandrost-4-en-3-one 586 mg of 17β-hydroxy-17α-methyl-7α-vinylandrost-4-en-3-one is reacted analogously to Example 14 to (Z)-17β-hydroxy-2-hydroxymethylene-17α-methyl-7α-vinylandrost-4-en-3-one. Yield: 357 mg as a foam.

Example 32

(Z)-17β-Hydroxy-2-hydroxymethylene-4α,17α-dimethyl-5α-androstan-3-one

Analogously to Example 14, 1 g of 17β-hydroxy-4α,17α-dimethyl-5α-androstan-3-one [DAS 1,134,371 (1962)] is reacted to (Z)-17β-hydroxy-2-hydroxymethylene-4α,17α-dimethyl-5α-androstan-3-one. Yield: 1 g as a foam.

PREPARATION OF THE STEROIDO[2,3-c]-1'H-PYRAZOLES

Example 33

17α-Methyl-1'H-androsta-4,15-dieno[3,2-c]pyrazol-17β-ol 1.8 g of (Z)-17β-hydroxy-2-hydroxymethylene-17α-methylandrosta-4,15-dien-3-one in 30 ml of ethanol is combined at room temperature with 0.6 ml of hydrazine (95%). After 1 hour, the reaction mixture is introduced into ice/water. The precipitated product is suctioned off, dissolved in ethyl acetate, washed with water, and dried, thus obtaining 1.8 g of crude 17α-methyl-1'H-androsta-4,15-dieno[3,2-c]pyrazol-17β-ol.

Example 34

4,17α-Dimethyl-1'H-androsta-4,15-dieno[3,2-c]pyrazol-17β-ol 2.7 g of (Z)-17β-hydroxy-2-hydroxymethylene-4,17α-dimethylandrosta-4,15-dien-3-one is reacted analogously to Example 33 to 4,17α-dimethyl-1'H-androsta-4,15-dieno[3,2-c]pyrazol-17β-ol. Yield: 1.3 g, mp 162° C.

Example 35

17α-Ethynyl-1'H-androsta-4,15-dieno[3,2-c]pyrazol-17β-ol

Analogously to Example 33, 5.4 g of (Z)-17α-ethynyl-17β-hydroxy-2-hydroxymethyleneandrosta-4,15-dien-3-one is reacted to 17α-ethynyl-1'H-androsta-4,15-dieno[3,2-c]pyrazol-17β-ol. Yield: 4.2 g as a crude product.

Example 36

17α-Ethynyl-4-methyl-1'H-androsta-4,15-dieno[3,2-c]pyrazol-17β-ol 4.5 g of (Z)-17α-ethynyl-17β-hydroxy-2-hydroxymethylene-4-methylandrosta-4,15-dien-3-one is reacted analogously to Example 33 to 17α-ethynyl-4-methyl-1'H-androsta-4,15-dieno[3,2-c]pyrazol-17β-ol. Yield: 3.4 g as a foam.

Example 37

17α-Chloroethynyl-1'H-androsta-4,15-dieno[3,2-c]pyrazol-17β-ol

Analogously to Example 33, 2.3 g of (Z)-17α-chloroethynyl-17β-hydroxy-2-hydroxymethyleneandrosta-4,15-dien-3-one is reacted to 17α-chloroethynyl-1'H-androsta-4,15-dieno[3,2-c]pyrazol-17β-ol. Yield: 2.1 g as a crude product.

Example 38

17α-Bromoethynyl-1'H-androsta-4,15-dieno[3,2-c]pyrazol-17β-ol

Analogously to Example 33, 1.9 g of (Z)-17α-bromoethynyl-17β-hydroxy-2-hydroxymethyleneandrosta-4,15-dien-3-one is reacted to 17α-bromoethynyl-1'H-androsta-4,15-dieno[3,2-c]pyrazol-17β-ol. Yield: 1.8 g as a crude product.

Example 39

17α-Propyn-1-yl-1'-androsta-4,15-dieno[3,2-c]pyrazol-17β-ol 1.3 g of (Z)-17β-hydroxy-2-hydroxymethylene-17α-propyn-1-ylandrosta-4,15-dien-3-one is reacted to 17α-propyn-1-yl-1'H-androsta-4,15-dieno[3,2-c]pyrazol-17β-ol as per Example 33. Yield: 1.2 g of crude product.

Example 40

17α-Methyl-6-methylene-1'H-androsta-4,15-dieno[3,2-c]pyrazol-17β-ol

Analogously to Example 33, 2.0 g of (Z)-17β-hydroxy-2-hydroxymethylene-17α-methyl-6-methyleneandrosta-4,15-dien-3-one is reacted to 17α-methyl-6-methylene-1'H-androsta-4,15-dieno[3,2-c]pyrazol-17β-ol. Yield: 1.4 g as a foam.

Example 41

17α-Methyl-6-methylene-1'H-androst-4-eno[3,2-c]pyrazol-17β-ol 2.1 g of (Z)-17β-hydroxy-2-hydroxymethylene-17α-methyl-6-methyleneandrost-4-en-3-one is reacted analogously to Example 33 to 17α-methyl-6-methylene-1'H-androst-4-eno[3,2-c]pyrazol-17β-ol. Yield: 1.9 g as a foam.

Example 42

6,6-Ethylene-17α-methyl-1'H-androst-4-eno[3,2-c]pyrazol-17β-ol 15.3 g of (Z)-6,6-ethylene-17β-hydroxy-2-hydroxymethylene-17α-methylandrost-4-en-3-one is reacted analogously to Example 33 to 6,6-ethylene-17α-methyl-1'H-androst-4-eno[3,2-c]pyrazol-17β-ol. Yield: 15.8 g as a foam.

Example 43

4,17α-Dimethyl-6-methylene-1'H-androst-4-eno[3,2-c]pyrazol-17β-ol 3.4 g of (Z)-17β-hydroxy-2-hydroxymethylene-4,17α-dimethyl-6-methyleneandrost-4-en-3-one is reacted analogously to Example 33 to 4,17α-dimethyl-6-methylene-1'H-androst-4-eno[3,2-c]pyrazol-17β-ol. Yield: 3.1 g of a crude product as a foam.

Example 44

7α,17α-Dimethyl-1'H-androst-4-eno[3,2-c]pyrazol-17β-ol

Analogously to Example 33, 1.8 g of (Z)-7α,17α-dimethyl-17β-hydroxy-2-hydroxymethyleneandrost-4-en-3-one is reacted to 7α,17α-dimethyl-1'H-androst-4-eno[3,2-c]pyrazol-17β-ol. Yield: 1.5 g of crude product as a foam.

Example 45

4,7α,17α-Trimethyl-1'H-androst-4-eno[3,2-c]pyrazol-17β-ol 405 mg of (Z)-17β-hydroxy-2-hydroxymethylene-4,7α,17α-trimethylandrost-4-en-3-one is reacted analogously to Example 33 to 4,7α,17α-trimethyl-1'H-androst-4-eno[3,2-c]pyrazol-17β-ol. Yield: 435 mg of crude product as a foam.

Example 46

7a-Methyl-17α-vinyl-1'H-androst-4-eno[3,2-c]pyrazol-17β-ol

Analogously to Example 33, 680 mg of (Z)-17β-hydroxy-2-hydroxymethylene-7α-methyl-17α-vinylandrost-4-en-3-one is reacted to 7α-methyl-17α-vinyl-1'H-androst-4-eno[3,2-c]pyrazol-17β-ol. Yield: 580 mg as a foam.

Example 47

17α-Methyl-15α,16α-methylene-1'H-androst-4-eno[3,2-c]pyrazol-17β-ol 970 mg of (Z)-17β-hydroxy-2-hydroxymethylene-17α-methyl-15α,16α-methyleneandrost-4-en-3-one is reacted analogously to Example 33 to 17α-methyl-15α,16α-methylene-1'H-androst-4-eno[3,2-c]pyrazol-17β-ol. Yield: 930 mg, mp 190°–200° C.

Example 48

17α-Methyl-11-methylene-1'H-androst-4-eno[3,2-c]pyrazol-17β-ol 800 mg of (Z)-17β-hydroxy-2-hydroxymethylene-17α-methyl-11-methyleneandrost-4-en-3-one is reacted analogously to Example 33 to 17α-methyl-11-methylene-1'H-androst-4-eno[3,2-c]pyrazol-17β-ol. Yield: 750 mg as a crude product.

Example 49

11β-Fluoro-17α-methyl-1'H-androst-4-eno[3,2-c]pyrazol-17β-ol 1.4 g of (Z)-11β-fluoro-17β-hydroxy-2-hydroxymethylene-17α-methylandrost-4-en-3-one is reacted analogously to Example 33 to 11β-fluoro-17α-methyl-1'H-androst-4-eno[3,2-c]pyrazol-17β-ol. Yield: 1.2 g as a crude product.

Example 50

17α-Methyl-7α-vinyl-1'H-androst-4-eno[3,2-c]pyrazol-17β-ol 357 mg of (Z)-17β-hydroxy-2-hydroxymethylene-17α-methyl-7α-vinylandrost-4-en-3-one is reacted analogously to Example 33 to 17α-methyl-7α-vinyl-1'H-androst-4-eno[3,2-c]pyrazol-17β-ol. Yield: 309 mg of a crude product.

Example 51

4α,17α-Dimethyl-1'H-5α-androstano[3,2-c]pyrazol-17β-ol

Analogously to Example 33, 1 g of (Z)-17β-hydroxy-2-hydroxymethylene-4α,17α-dimethyl-5α-androstan-3-one is reacted to 4α,17α-dimethyl-1'H-5α-androstano[3,2-c]pyrazol-17β-ol. Yield: 950 mg of a crude product.

PREPARATION OF THE 1'-ACYL- AND 1'-MESYL-STEROIDO[3,2-c]PYRAZOLES

Example 52

1'-Mesyl-17α-methyl-1'H-androsta-4,15-dieno[3,2-c]pyrazol-17β-ol

At 0° C., 0.5 ml of methanesulfonyl chloride is added dropwise to 1.6 g of 17α-methyl-1'H-androsta-4,15-dieno[3,2-c]pyrazol-17β-ol in 10 ml of pyridine. After 30 minutes, the reaction mixture is stirred into ice/water. The precipitated product is suctioned off, dissolved in methylene chloride, washed with water, dried, and concentrated under vacuum. After chromatography of the crude product on silica gel with a hexane-ethyl acetate gradient, 1.0 g of 1'-mesyl-17α-methyl-1'H-androsta-4,15-dieno[3,2-c]pyrazol-17β-ol is obtained, mp 198° C. (from acetone/hexane).

Example 53

1'-Mesyl-4,17α-dimethyl-1'H-androsta-4,15-dieno[3,2-c]pyrazol-17β-ol 2.2 g of 4,17α-dimethyl-1'H-androsta-4,15-dieno[3,2-c]pyrazol-17β-ol is reacted analogously to Example 52 to 1'-mesyl-4,17α-dimethyl-1'H-androsta-4,15-dieno[3,2-c]pyrazol-17β-ol. Yield: 1.6 g, mp 218° C. (from acetone/hexane).

Example 54

17α-Ethynyl-1'-mesyl-1'H-androsta-4,15-dieno[3,2-c]pyrazol-17β-ol 3.1 g of 17α-ethynyl-1'H-androsta-4,15-dieno[3,2-c]pyrazol-17β-ol is reacted analogously to Example 52 to 17α-ethynyl-1'-mesyl-1'H-androsta-4,15-dieno[3,2-c]pyrazol-17β-ol. Yield.: 1.2 g, mp 246° C. (from acetone/hexane).

Example 55

17α-Ethynyl-1'-mesyl-4-methyl-1'H-androsta-4,15-dieno[3,2-c]pyrazol-17β-ol

Analogously to Example 52, 1.3 g of 17α-ethynyl-4-methyl-1'H-androsta-4,15-dieno[3,2-c]pyrazol-17β-ol is reacted to 17α-ethynyl-1'-mesyl-4-methyl-1'H-androsta-4,15-dieno[3,2-c]pyrazol-17β-ol. Yield: 250 mg as a foam.

Example 56

17α-Chloroethynyl-1'-mesyl-1'H-androsta-4,15-dieno[3,2-c]pyrazol-17β-ol 1.8 g of 17α-chloroethynyl-1'H-androsta-4,15-dieno[3,2-c]pyrazol-17β-ol is reacted analogously to Example 52 to 17α-chloroethynyl-1'-mesyl-1'H-androsta-4,15-dieno[3,2-c]pyrazo-17β-ol. Yield: 980 mg as a foam.

Example 57

17α-Bromoethynyl-1'-mesyl-1'H-androsta-4,15-dieno[3,2-c]pyrazol-17β-ol 1.3 g of 17α-bromoethynyl-1'H-androsta-4,15-dieno[3,2-c]pyrazol-17β-ol is reacted analogously to Example 52 to 17α-bromoethynyl-1'-mesyl-1'H-androsta-4,15-dieno[3,2-c]pyrazol-17β-ol. Yield: 80 mg as a foam.

Example 58

1'-Mesyl-17α-propyn-1-yl-1'H-androsta-4,15-dieno[3,2-c]pyrazol-17β-ol 800 mg of 17α-propyn-1-yl-1'H-androsta-4,15-dieno[3,2-c]pyrazol-17β-ol is reacted analogously to Example 52 to 1'-mesyl-17α-propyn-1-yl-1'H-androsta-4,15-dieno[3,2-c]pyrazol-17β-ol. Yield: 340 mg as a foam.

Example 59

1'-Acetoxy-17α-methyl-1'H-androsta-4,15-dieno[3,2-c]pyrazol-17β-ol

At room temperature, 0.5 ml of acetic acid anhydride is added dropwise to 1.1 g of 17α-methyl-1'H-androsta-4,15-dieno[3,2-c]pyrazol-17β-ol in 7 ml of pyridine. After 30 minutes, the reaction mixture is stirred into ice/water. The precipitated product is suctioned off, dissolved in ethyl acetate, washed with water, dried, and concentrated under vacuum. After chromatography of the crude product on silica gel with a hexane-ethyl acetate gradient, 530 mg of 1'-acetoxy-17α-methyl-1'H-androsta-4,15-dieno[3,2-c]pyrazol-17β-ol is obtained as a foam.

Example 60

1'-Acetoxy-4,17α-dimethyl-1'H-androsta-4,15-dieno[3,2-c]pyrazol-17β-ol 950 mg of 4,17α-dimethyl-1'H-androsta-4,15-dieno[3,2-c]pyrazol-17β-ol is reacted analogously to Example 59 with acetic anhydride to 1'-acetoxy-4,17α-dimethyl-1'H-androsta-4,15-dieno[3,2-c]pyrazol-17β-ol. Yield: 370 mg as a foam.

Example 61

1'-Mesyl-17α-methyl-6-methylene-1'H-androsta-4,15-dieno[3,2-c]pyrazol-17β-ol

Analogously to Example 52, 860 mg of 17α-methyl-6-methylene-1'H-androsta-4,15-dieno[3,2-c]pyrazol-17β-ol is reacted to 1'-mesyl-17α-methyl-6-methylene-1'H-androsta-4,15-dieno[3,2-c]pyrazol-17β-ol. Yield: 210 mg as a foam.

Example 62

1'-Mesyl-17α-methyl-6-methylene-1'H-androst-4-eno[3,2-c]pyrazol-17β-ol 1.9 g of 17α-methyl-6-methylene-1'H-androst-4-eno[3,2-c]pyrazol-17β-ol is reacted analogously to Example 52 to 1'-mesyl-17α-methyl-6-methylene-1'H-androst-4-eno[3,2-c]pyrazol-17β-ol. Yield: 742 mg, mp 190° C. (decomposition, from isopropyl ether).

Example 63

6,6-Ethylene-1'-mesyl-17α-methyl-1'H-androst-4-eno[3,2-c]pyrazol-17β-ol 17.1 g of 6,6-ethylene-17α-methyl-1'H-androst-4-eno[3,2-c]pyrazol-17β-ol is reacted analogously to Example 52 to 6,6-ethylene-1'-mesyl-17α-methyl-1'H-androst-4-eno[3,2-c]pyrazol-17β-ol. Yield: 8.1 g, mp 195°–196° C. (from isopropyl ether).

Example 64

1'-Mesyl-4,17α-dimethyl-6-methylene-1'H-androst-4-eno[3,2-c]pyrazol-17β-ol 1.7 g of 4,17α-dimethyl-6-methylene-1'H-androst-4-eno[3,2-c]pyrazol-17β-ol is reacted analogously to Example 52 to 1'-mesyl-4,17α-dimethyl-6-methylene-1'H-androst-4-eno[3,2-c]pyrazol-17β-ol. Yield: 850 mg as a foam.

Example 65

1'-Mesyl-7α,17α-dimethyl-1'H-androst-4-eno[3,2-c]pyrazol-17β-ol 1.4 g of 7α,17α-dimethyl-1'H-androst-4-eno[3,2-c]pyrazol-17β-ol is reacted analogously to Example 52 to 1'-mesyl-7α,17α-dimethyl-1'H-androst-4-eno[3,2-c]pyrazol-17β-ol. Yield: 940 mg, mp 191°–192° C. (from isopropyl ether).

Example 66

1'-Mesyl-4,7α,17α-trimethyl-1'H-androst-4-eno[3,2-c]pyrazol-17β-ol 430 mg of 4,7α,17α-trimethyl-1'H-androst-4-eno[3,2-c]pyrazol-17β-ol is reacted analogously to Example 52 to 1'-mesyl-4,7α,17α-trimethyl-1'H-androst-4-eno[3,2-c]pyrazol-17β-ol. Yield: 290 mg, mp 210° C. (from isopropyl ether).

Example 67

1'-Mesyl-7α-methyl-17α-vinyl-1'H-androst-4-eno[3,2-c]pyrazol-17β-ol 640 mg of 7α-methyl-17α-vinyl-1'H-androst-4-eno[3,2-c]pyrazol-17β-ol is reacted analogously to Example 52 to 1'-mesyl-7α-methyl-17α-vinyl-1'H-androst-4-eno[3,2-c]pyrazol-17β-ol. Yield: 290 mg as a foam.

Example 68

1'-Mesyl-17α-methyl-15α,16α-methylene-1'H-androst-4eno[3,2-c]pyrazol-17β-ol 840 mg of 17α-methyl-15α,16α-methylene-1'H-androst-4-eno[3,2-c]pyrazol-17β-ol is reacted analogously to Example 52 to 1'-mesyl-17α-methyl-15α,16α-methylene-1'H-androst-4-eno[3,2-c]pyrazol-17β-ol. Yield: 450 mg, mp 199° C. (decomposition).

Example 69

1'-Mesyl-17α-methyl-11-methylene-1'H-androst-4-eno[3,2-c]pyrazol-17β-ol

Analogously to Example 52, 320 mg of 17α-methyl-11-methylene-1'H-androst-4-eno[3,2-c]pyrazol-17β-ol is reacted to 1'-mesyl-17α-methyl-11-methylene-1'H-androst-4-eno[3,2-c]pyrazol-17β-ol. Yield: 130 mg as a foam.

Example 70

11β-Fluoro-1'-mesyl-17α-methyl-1'H-androsteno[3,2-c]pyrazol-17β-ol

Analogously to Example 52, 530 mg of 11β-fluoro-17α-methyl-1'H-androst-4-eno[3,2-c]pyrazol-17β-ol is reacted to 11β-fluoro-1'-mesyl-17α-methyl-1'H-androsteno[3,2-c]pyrazol-17β-ol. Yield: 310 mg as a foam.

Example 71

1'-Mesyl-17α-methyl-7α-vinyl-1'H-androst-4-eno[3,2-c]pyrazol-17β-ol 300 mg of 17α-methyl-7α-vinyl-1'H-androst-4-eno[3,2-c]pyrazol-17β-ol is reacted analogously to Example 52 to 1'-mesyl-17α-methyl-7α-vinyl-1'H-androst-4-eno[3,2-c]pyrazol-17β-ol. Yield: 133 mg, mp 175°–176° C. (from isopropyl ether).

Example 72

1'-Mesyl-4α,17α-dimethyl-1'H-5α-androstano[3,2-c]pyrazol-17β-ol 1.1 g of 4α,17α-dimethyl-1'H-5α-androstano[3,2-c]pyrazol-17β-ol is reacted analogously to Example 52 to 1'-mesyl-4α,17α-dimethyl-1'H-5α-androstano[3,2-c]pyrazol-17β-ol. Yield: 945 mg, mp 197°–198° C. (from isopropyl ether).

PREPARATION OF THE MESYLTRIAZOLES

Example 73

2'-Mesyl 4,17α-dimethyl-2'H-triazolo[4',5':2,3]androst-4-en-17β-ol (a) 17β-Hydroxy-2-hydroxyimino-4,17α-dimethylandrost-4-en-3-one 25 g of sodium nitrite in 50 ml of water is added to 25 g of (Z)-17β-hydroxy-2-hydroxymethylene-4,17α- dimethylandrost-4-en-3-one [U.S. Pat. No. 3,704,295 (1972)] in 200 ml of tetrahydrofuran and 200 ml of methanol. Subsequently, within 15 minutes, 43.7 ml of glacial acetic acid is added dropwise at 15°–20° C. After 1 hour, the reaction mixture is stirred into ice/water. The precipitated product is suctioned off, dissolved in methylene chloride, washed with water, dried, and concentrated under vacuum. The crude product yields, after chromatography on silica gel with a methylene chloride-acetone gradient, 25 g of 17β-hydroxy-2-hydroxyimino-4,17α-dimethylandrost-4-en-3-one, mp 198°–200° C. (from isopropyl ether).

(b) 2-Hydroxyimino-3-mesylhydrazono-4,17α-dimethylandrost-4-en-17β-ol

At room temperature, 20 g of 17β-hydroxy-2-hydroxyimino-4,17α-dimethylandrost-4-en-3-one in 500 ml of methanol is combined with 7 g of methanesulfonyl hydrazide and 1.6 ml of concentrated hydrochloric acid. After 24 hours, 3 g of sodium acetate is added, the solvent is extensively distilled off under vacuum, the reaction product is dissolved in diethyl ether, washed with water, dried, and concentrated under vacuum. After chromatography of the crude product on silica gel with a methylene chloride-acetone gradient, 16 g of 2-hydroxyimino-3-mesylhydrazono-4,17α-dimethylandrost-4-en-17β-ol is obtained as the crude product.

(c) 2'-Mesyl-4,17α-dimethyl-2'H-triazolo[4',5':2,3]androst-4-en-17β-ol 16 g of 2-hydroxyimino-3-mesylhydrazono-4,17α-dimethylandrost-4-en-17β-ol is combined in 160 ml of pyridine at room temperature with 8 ml of methanesulfonic acid chloride. After 3.5 hours, 1.8 ml of water is added under ice/water cooling, the mixture is stirred for 30 minutes, and then the reaction mixture is poured into ice/water. The precipitated product is suctioned off, dissolved in ethyl acetate, washed with water, dried, and concentrated under vacuum. The crude product is chromatographed on silica gel with a methylene chloride-(methyl tert-butyl ether) gradient. Yield: 10.2 g of 2'-mesyl-4,17α-dimethyl-2'H-triazolo[4',5':2,-3]androst-4-en-17β-ol, mp 190°–191° C. (decomposition, from isopropyl ether).

Example 74

2'-Mesyl-17α-methyl-2'H-triazolo[4',5':2,3]androst-4-en-17β-ol (a) 17β-Hydroxy-2-hydroxyimino-17α-methylandrost-4-en-3-one Analogously to Example 73(a), 1.8 g of (Z)-17β-hydroxy-2-hydroxymethylene-17α-methylandrost-4-en-3-one is reacted to 17β-hydroxy-2-hydroxyimino-17α-methylandrost-4-en-3-one. Yield: 880 mg as a crude product.

(b) 2-Hydroxyimino-3-mesylhydrazono-17α-methylandrost-4-en-17β-ol 800 mg of 17β-hydroxy-2-hydroxyimino-17α-methylandrost-4-en-3-one is reacted analogously to Example 73(b) to 2-hydroxyimino-3-mesylhydrazono-17α-methylandrost-4-en-17β-ol. Yield: 665 mg as a crude product.

(c) 2'-Mesyl-17α-methyl-2'H-triazolo[4',5':2,3]androst-4-en-17β-ol 490 mg of 2-hydroxyimino-3-mesylhydrazono-17α-methylandrost-4-en-17β-ol is reacted analogously to Example 73(c) to 2'-mesyl-17α-methyl-2'H-triazolo[4',5':2,3]androst-4-en-17β-ol. Yield: 235 mg, mp 198°–204° C. (decomposition, from isopropyl ether).

Example 75

2'-Mesyl-17α-methyl-2'H-triazolo[4',5':2,3]androsta-4,15-dien-17β-ol (a) 17β-Hydroxy-2-hydroxyimino-17α-methylandrosta-4,15-dien-3-one 1.2 g of (Z)-17β-hydroxy-2-hydroxymethylene-17α-methylandrosta-4,15-dien-3-one is reacted analogously to Example 73(a) to 17β-hydroxy-2-hydroxyimino-17α-methylandrosta-4,15-dien-3-one. Yield: 1 g as a crude product.

(b) 2-Hydroxyimino-3-mesylhydrazono-17α-methylandrosta-4,15-dien-17β-ol 538 mg of 17β-hydroxy-2-hydroxyimino-17α-methylandrosta-4,15-dien-3-one is reacted analogously to Example 73(b) to 2-hydroxyimino-3-mesylhydrazono-17α-methylandrosta-4,15-dien-17β-ol. Yield: 260 mg as a crude product.

(c) 2'-Mesyl-17α-methyl-2'H-triazolo[4',5':2,3]androsta-4,15-dien-17β-ol 430 mg of 2-hydroxyimino-3-mesylhydrazono-17α-methylandrosta-4,15-dien-17β-ol is reacted analogously to Example 73(c) to 2'-mesyl-17α-methyl-2'H-triazolo[4',5':2,3]androsta-4,15-dien-17β-ol. Yield: 116 mg, mp 180°–181° C. (from isopropyl ether).

Example 76

2'-Mesyl-4,17α-dimethyl-2'H-triazolo[4',5':2,3]androsta-4,15-dien-17β-ol (a) 17β-Hydroxy-2-hydroxyimino-4,17α-dimethylandrosta-4,15-dien-3-one 860 mg of (Z)-17β-hydroxy-2-hydroxymethylene-4,17α-dimethylandrosta-4,15-dien-3-one is reacted analogously to Example 73(a) to 17β-hydroxy-2-hydroxyimino-4,17α-dimethylandrosta-4,15-dien-3-one. Yield: 560 mg as a crude product.

(b) 2-Hydroxyimino-3-mesylhydrazono-4,17α-dimethylandrosta-4,15-dien-17β-ol 540 mg of 17β-hydroxy-2-hydroxyimino-4,17α-dimethylandrosta-4,15-dien-3-one is reacted analogously to Example 73(b) to 2-hydroxyimino-3-mesylhydrazono-4,17α-dimethylandrosta-4,15-dien-17β-ol. Yield: 213 mg as a crude product.

(c) 2'-Mesyl-4,17α-dimethyl-2'H-triazolo[4',5':2,3]androsta-4,15-dien-17β-ol 200 mg of 2-hydroxyimino-3-mesylhydrazono-4,17α-dimethylandrosta-4,15-dien-17β-ol is reacted analogously to Example 73(c) to 2'-mesyl-4,17α-dimethyl-2'H-triazolo[4',5':2,3]androsta-4,15-dien-17β-ol. Yield: 57 mg, mp 171°–173° C. (decomposition, from isopropyl ether).

Example 77

6,6-Ethylene-2'-mesyl-17α-methyl-2'H-triazolo[4',5':2,-3]androst-4-en-17β-ol (a) 6,6-Ethylene-17β-hydroxy-2-hydroxyimino-17α-methylandrost-4-en-3-one 3.8 g of (Z)-6,6-ethylene-17β-hydroxy-2-hydroxymethylene-17α-methylandrost-4-en-3-one is reacted analogously to Example 73(a) to 6,6-ethylene-17β-hydroxy-2-hydroxyimino-17αmethylandrost-4-en-3one. Yield: 2.6 g as a crude product.

(b) 6,6-Ethylene-2-hydroxyimino-3-mesylhydrazono-17α-methylandrost-4-en-17β-ol 2.5 g of 6,6-ethylene-17β-hydroxy-2-hydroxyimino-17α-methylandrost-4-en-3-one is reacted analogously to Example 73(b) to 6,6-ethylene-2-hydroxyimino-3-mesylhydrazono-17α-methylandrost-4-en-17βol. Yield: 1.6 g as a crude product.

(c) 6,6-Ethylene-2'-mesyl-17α-methyl-2'H-triazolo[4',5':2,3]androst-4-en-17β-ol 1.5 g of 6,6-ethylene-2-hydroxyimino-3-mesylhydrazono-17α-methylandrost-4-en-17β-ol is reacted analogously to Example 73(c) to 6,6-ethylene-2'-mesyl-17α-methyl-2'H-triazolo[4',5':2,3]androst-4-en-17β-ol. Yield: 770 mg, mp 195°–196° C. (decomposition, from isopropyl ether).

Example 78

2'-Mesyl-17α-methyl-7α-vinyl-2'H-triazolo[4',5':2,3]androst-4-en-17β-ol (a) 17β-Hydroxy-2-hydroxyimino-17α-methyl-7α-vinylandrost-4-en-3-one 1.3 g of (Z)-17β-hydroxy-2-hydroxymethylene-17α-methyl-7α-vinylandrost-4-en-3-one is reacted analogously to Example 73(a) to 17β-hydroxy-2-hydroxyimino-17α-methyl-7α-vinylandrost-4-en-3-one. Yield: 990 mg as a crude product.

(b) 2-Hydroxyimino-3-mesylhydrazono-17α-methyl-7α-vinylandrost-4-en-17β-ol 990 mg of 17β-hydroxy-2-hydroxyimino-17α-methyl-7α-vinylandrost-4-en-3-one is reacted analogously to Example 73(b) to 2-hydroxyimino-3-mesylhydrazono-17α-methyl-7α-vinylandrost-4-en-17β-ol. Yield: 500 mg as a crude product.

(c) 2'-Mesyl-17α-methyl-7α-vinyl-2'H-triazolo[4',5':2,3]androst-4-en-17β-ol 500 mg of 2-hydroxyimino-3-mesylhydrazono-17α-methyl-7α-vinylandrost-4-en-17β-ol is reacted analogously to Example 73(c) to 2'-mesyl-17α-methyl-7α-vinyl-2'H-triazolo[4',5':2,3]androst-4-en-17β-ol. Yield: 306 mg as a foam.

Example 79

2'-Mesyl-7α,17α-dimethyl-2'H-triazolo[4',5':2,3]androst-4-en-17β-ol (a) 17β-Hydroxy-2-hydroxyimino-7α,17α-dimethylandrost-4-en-3-one 3.3 g of (Z)-17β-hydroxy-2-hydroxymethylene-7α,17α-dimethylandrost-4-en-3-one is reacted analogously to Example 73(a) to 17β-hydroxy-2-hydroxyimino-7α,17αdimethylandrost-4-en-3-one. Yield: 3.1 g as a crude product.

(b) 2-Hydroxyimino-3-mesylhydrazono-7α,17α-dimethylandrost-4-en-17β-ol 1 g of 17β-hydroxy-2-hydroxyimino-7α,17α-dimethylandrost-4-en-3-one is reacted analogously to Example 73(b) to 2-hydroxyimino-3-mesylhydrazono-7α,17α-dimethylandrost-4-en-17β-ol. Yield: 820 mg as a crude product.

(c) 2'-Mesyl-7α,17α-dimethyl-2'H-triazolo[4',5':2,3]androst-4-en-17β-ol 810 mg of 2-hydroxyimino-3-mesylhydrazono-7α,17α-dimethylandrost-4-en-17β-ol is reacted analogously to Example 73(c) to 2'-mesyl-7α,17α-dimethyl-2'H-triazolo[4',5':2,3]androst-4-en-17β-ol. Yield: 306 mg, mp 163°–164° C. (from isopropyl ether).

Example 80

2'-Mesyl-17α-methyl-2'H-triazolo[4',5':2,3]androsta-4,6-dien-17β-ol (a) 17β-Hydroxy-2-hydroxyimino-17α-methylandrosta-4,6-dien-3-one 4 g of (Z)-17β-hydroxy-2-hydroxymethylene-17α-methylandrosta-4,6-dien-3-one [U.S. Pat. No. 3,704,295 (1972)] is reacted analogously to Example 73(a) to 17β-hydroxy-2-hydroxyimino-17α-methylandrosta-4,6-dien-3-one. Yield: 3.6 g as a crude product.

(b) 2-Hydroxyimino-3-mesylhydrazono-17α-methylandrosta-4,6-dien-17β-ol 3.5 g of 17β-hydroxy-2-hydroxyimino-17α-methylandrosta-4,6-dien-3-one is reacted analogously to Example 73(b) to 2-hydroxyimino-3-mesylhydrazono-17α-methylandrosta-4,6-dien-17β-ol. Yield: 3 g as a crude product.

(c) 2'-Mesyl-17α-methyl-2'H-triazolo[4',5':2,3]androsta-4,6-dien-17β-ol 9 g of 2-hydroxyimino-3-mesylhydrazono-17α-methylandrosta-4,6-dien-17β-ol is reacted analogously to Example 73(c) to 2'-mesyl-17α-methyl-2'H-triazolo[4',5':2,3]androsta-4,6-dien-17β-ol. Yield: 2.1 g, mp 205°–206° C. (from isopropyl ether).

Example 81

2'-Mesyl-17α-methyl-11-methylene-2'H-triazolo[4',5':2,3]androst-4-en-17β-ol (a) 17β-Hydroxy-2-hydroxyimino-17α-methyl-11-methyleneandrost-4-en-3-one 2.8 g of (Z)-17β-hydroxy-2-hydroxymethylene-17α-methyl-11-methyleneandrost-4-en-3-one is reacted analogously to Example 73(a) to 17β-hydroxy-2-hydroxyimino-17α-methyl-11-methyleneandrost-4-en-3-one. Yield: 1.4 g as a crude product.

(b) 2-Hydroxyimino-3-mesylhydrazono-17α-methyl-11-methyleneandrost-4-en-17β-ol 1.2 g of 17β-hydroxy-2-hydroxyimino-17α-methyl-11-methyleneandrost-4-en-3-one is reacted analogously to Example 73(b) to 2-hydroxyimino-3-mesylhydrazono-17α-methyl-11-methyleneandrost-4-en-17β-ol. Yield: 860 mg as a crude product.

(c) 2'-Mesyl-17α-methyl-11-methylene-2'H-triazolo[4',5':2,3]androst-4-en-17β-ol 790 mg of 2-hydroxyimino-3-mesylhydrazono-17α-methyl-11-methyleneandrost-4-en-17β-ol is reacted analogously to Example 73(c) to 2'-mesyl-17α-methyl-11-methylene-2'H-triazolo[4',5':2,3]androst-4-en-17β-ol. Yield: 410 mg as a foam.

Example 82

11β-Fluoro-2'-Mesyl-17α-methyl-2'H-triazolo[4',5':2,3]androst-4-en-17β-ol (a) 11β-Fluoro-17β-hydroxy-2-hydroxyimino-17α-methylandrost-4-en-3-one 2.1 g of (Z)-11β-fluoro-17β-hydroxy-2-hydroxymethylene-17α-methylandrost-4-en-3-one is reacted analogously to Example 73(a) to 11β-fluoro-17β-hydroxy-2-hydroxyimino-17α-methylandrost-4-en-3-one. Yield: 1.1 g as a crude product.

(b) 11β-Fluoro-2-hydroxyimino-3-mesylhydrazono-17α-methylandrost-4-en-17β-ol 1 g of 11β-fluoro-17β-hydroxy-2-hydroxyimino-17α-methylandrost-4-en-3-one is reacted analogously to Example 73(b) to 11β-fluoro-2-hydroxyimino-3-mesylhydrazono-17α-methylandrost-4-en-17β-ol. Yield: 710 mg as a crude product.

(c) 11β-Fluoro-2'-mesyl-17α-methyl-2'H-triazolo[4',5':2,3]androst-4-en-17β-ol 560 mg of 11β-fluoro-2-hydroxyimino-3-mesylhydrazono-17α-methylandrost-4-en-17β-ol is reacted analogously to Example 73(c) to 11β-fluoro-2'-mesyl-17α-methyl-2'H-triazolo[4',5':2,3]androst-4-en-17β-ol. Yield: 210 mg as a foam.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A triazole steroid of formula I

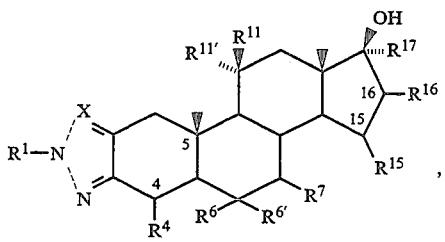

wherein
X is a nitrogen atom,
$R^1$ is an alkylsulfonyl group R—$SO_2$— wherein R is an alkyl group of 1-3 carbon atoms,

is a C—C single or double bond,
$R^4$ is a hydrogen atom or a methyl group that is in the α- or β-position in case of a $C_4$-$C_5$ single bond,
$R^6$ and $R^{6'}$ in each case are a hydrogen atom or jointly a 6,6-methylene or ethylene group,
$R^7$ is a hydrogen atom or, if $R^6$ and $R^{6'}$ are respectively hydrogen atoms, additionally a saturated or unsaturated α- or β-alkyl group of 1-4 carbon atoms, or
$R^6$ and $R^7$ are a 6α,7α- or 6β,7β-methylene group or an additional bond between the number 6 and 7 carbon atoms, and also
$R^{6'}$ is a hydrogen atom,
$R^{11}$ is a hydrogen, fluorine or chlorine atom, and
$R^{11'}$ is a hydrogen atom, or
$R^{11}$ and $R^{11'}$ jointly are a methylene group,
$R^{15}$ and $R^{16}$ each are a hydrogen atom,

is a C—C double bond, a 15α,16α- or a 15β,16β-methylene group, or a C—C single bond, and also
$R^{17}$ is a hydrogen atom, an alkyl group of 1-4 carbon atoms, a vinyl, E- or Z-halovinyl, allyl, ethynyl, bromoethynyl, chloroethynyl, or propynyl group, wherein halo is F, Cl, Br or I.

2. A triazole of claim 1, wherein $C_4$-$C_5$ is a double bond.

3. A triazole of claim 2, wherein $C_{15}$-$C_{16}$ is a double bond.

4. A triazole of claim 1, wherein $R^1$ is a methylsulfonyl group.

5. A triazole of claim 1, wherein $R^{17}$ is —$CH_3$ at the α-position.

6. A triazole of claim 1, wherein $R^{11}$ is fluorine.

7. A triazole of claim 1, wherein $R^6$ and $R^{6'}$ are jointly 6,6-ethylene.

8. A triazole of claim 1, wherein $R^7$ is a methyl or vinyl group.

9. A triazole of claim 1, wherein $R^{11}$ and $R^{11'}$ are jointly a methylene group.

10. A triazole which is
2'-mesyl-4,17α-dimethyl-2'H-triazolo[4',5':2,3]androst-4-en-17β-ol,
2'-mesyl-17α-methyl-2'H-triazolo[4',5':2,3]androst-4-en-17β-ol,
2'-mesyl-17α-methyl-2'H-triazolo[4',5':2,3]androsta-4,15-dien-17β-ol,
2'-mesyl-4,17α-dimethyl-2'H-triazolo[4',5':2,3]androsta-4,15-dien-17β-ol,
6,6-ethylene-2'-mesyl-17α-methyl-2'H-triazolo[4',5':2,3]androst-4-en-17β-ol,
2'-mesyl-17α-methyl-7α-vinyl-2'H-triazolo[4',5':2,3]androst-4-en-17β-ol,
2'-mesyl-7α,17α-dimethyl-2'H-triazolo[4',5':2,3]androst-4-en-17β-ol,
2'-mesyl-17α-methyl-2'H-triazolo[4',5':2,3]androsta-4,6-dien-17β-ol,
2'-mesyl-17α-methyl-11-methylene-2'H-triazolo[4',5':2,3]androst-4-en-17β-ol, or
11β-fluoro-2'-mesyl-17α-methyl-2'H-triazolo[4',5':2,3]androst-4-en-17β-ol.

11. A pharmaceutical composition comprising an effective amount of a compound of claim 1 and a pharmaceutically acceptable carrier.

12. A method of treating benign prostatic hyperplasia comprising administering an effective amount of a compound of claim 1.

13. A method of treating an androgen-dependent disorder or disease comprising administering an effective amount of a compound of claim 1.

14. A method of treating androgen-dependent prostatic carcinoma comprising administering an effective amount of a compound of claim 1.

* * * * *